United States Patent
Li et al.

(10) Patent No.: US 11,773,087 B2
(45) Date of Patent: Oct. 3, 2023

(54) GLP-1R RECEPTOR AGONIST COMPOUND AND USE THEREOF

(71) Applicant: SUZHOU VINCENTAGE PHARMA CO., LTD, Jiangsu (CN)

(72) Inventors: Ben Li, Jiangsu (CN); Shanghai Yu, Jiangsu (CN)

(73) Assignee: SUZHOU VINCENTAGE PHARMA CO., LTD, Jiangsu (CN)

( * ) Notice: Subject to any disclaimer, the term of this patent is extended or adjusted under 35 U.S.C. 154(b) by 0 days.

(21) Appl. No.: 18/192,735

(22) Filed: Mar. 30, 2023

(65) Prior Publication Data

US 2023/0257369 A1    Aug. 17, 2023

Related U.S. Application Data

(63) Continuation of application No. PCT/CN2021/123505, filed on Oct. 13, 2021.

(30) Foreign Application Priority Data

Dec. 3, 2020 (CN) .......................... 202011406013.0
Mar. 29, 2021 (CN) .......................... 202110334388.9

(51) Int. Cl.
| | | |
|---|---|---|
| C07D 405/14 | (2006.01) | |
| C07D 405/06 | (2006.01) | |
| C07D 401/06 | (2006.01) | |
| C07D 401/14 | (2006.01) | |
| C07D 471/04 | (2006.01) | |
| A61P 3/10 | (2006.01) | |

(52) U.S. Cl.
CPC ............. C07D 405/14 (2013.01); A61P 3/10 (2018.01); C07D 401/06 (2013.01); C07D 401/14 (2013.01); C07D 405/06 (2013.01); C07D 471/04 (2013.01); C07B 2200/05 (2013.01)

(58) Field of Classification Search
CPC ................ C07D 405/14; C07D 401/06; C07D 401/14; C07D 405/06; C07D 471/04; A61P 3/10; C07B 2200/05
See application file for complete search history.

(56) References Cited

U.S. PATENT DOCUMENTS

| | | |
|---|---|---|
| 2008/0293684 A1 | 11/2008 | Pinkerton et al. |
| 2008/0312271 A1 | 12/2008 | Efremov et al. |
| 2009/0192169 A1 | 7/2009 | Egle et al. |

FOREIGN PATENT DOCUMENTS

| | | | |
|---|---|---|---|
| CN | 1993326 A | 7/2007 | |
| CN | 101454292 A | 6/2009 | |
| WO | 2008012623 A1 | 1/2008 | |
| WO | 2018109607 A1 | 6/2018 | |
| WO | 2019239371 A1 | 12/2019 | |
| WO | WO-2019239371 A1 * | 12/2019 | ......... A61K 31/4427 |

OTHER PUBLICATIONS

Griffith et al., "A small-molecule oral agonist of the human glucagon-line peptide-1 receptor" bioRxiv preprint, posted Sep. 30, 2020. (Year: 2020).*
Jan. 18, 2022 International Search Report issued in International Patent Application No. PCT/CN2021/123505.
Jan. 18, 2022 Written Opinion of the International Searching Authority issued in International Patent Application No. PCT/CN2021/123505.
David A. Griffith. "A Small-Molecule Oral Agonist of the Human Glucagon-like Peptide-1 Receptor" J. Med. Chem. 2022, 65, 12, 8208-8226.

* cited by examiner

Primary Examiner — Michael Barker
Assistant Examiner — Jed A Kucharczk
(74) Attorney, Agent, or Firm — Houston Beshining Law Office PLLC; Liangang Ye

(57) ABSTRACT

The present invention relates to a GLP-1R receptor agonist compound and a use thereof. Specifically, the present invention discloses a compound represented by formula (I) or a pharmaceutically acceptable salt thereof. The compound can be used for treating a metabolism-related disease, such as diabetes or nonalcoholic fatty liver disease, by means of activating GLP-1R receptors.

(I)

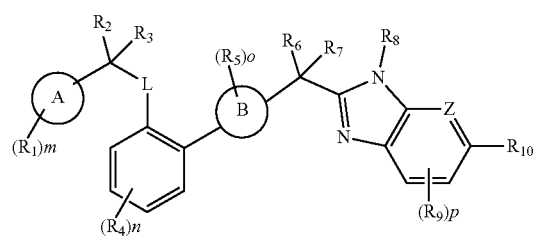

14 Claims, No Drawings

GLP-1R RECEPTOR AGONIST COMPOUND AND USE THEREOF

CROSS-REFERENCE TO RELATED APPLICATIONS

The present application is a continuation application of International Application No. PCT/CN2021/123505, filed on Oct. 13, 2021, which claims the right of the priorities for invention patent application with the title of "GLP-1R receptor agonist compound and use thereof" and the application number of 202011406013.0 submitted to the Chinese Patent Office on Dec. 3, 2020 and invention patent application with the title of "GLP-1R receptor agonist compound and use thereof" and the application number of 202110334388.9 submitted to the Chinese Patent Office on Mar. 29, 2021, which are incorporated herein by reference.

TECHNICAL FIELD

The present disclosure relates to the field of drug synthesis, in particular to a class of GLP-1R receptor agonist compounds and a use thereof.

BACKGROUND

GLP-1 receptor (GLP-1R), is a member of the glucagon receptor subfamily in the G-protein coupled receptor B family (secretin family) of a 7-time transmembrane, and it is widely distributed in pancreas and extra-pancreatic tissues, such as central nervous system, cardiovascular, gastrointestinal tract, lung, kidney, thyroid, skin, lymphocyte, mesenchymal stem cells, etc.

Glucagon-like peptide-1 (GLP-1) is a natural ligand of the GLP-1R receptor and is a polypeptide compound. It has two forms, namely GLP-1 (7-37) and GLP-1 (7-36) amide, which differ only by one amino acid sequence. About 80% of the circulating activity of GLP-1 comes from GLP-1 (7-36) amide. GLP-1 is expressed by the proglucagon gene. In islet α cells, the main expression product of the proglucagon gene is glucagon, while in the L cells of the intestinal mucosa, the prohormone convertase 1 (PC1) cleaves proglucagon to its carboxy-terminal peptide chain sequence, namely GLP-1. The combination of GLP-1 and GLP-1R receptor can promote the synthesis and secretion of insulin, and also stimulate the proliferation of p cells and inhibit their apoptosis.

GLP-1 exerts the hypoglycemic effect mainly through the following aspects.

1) Protection of Islet β Cells

GLP-1 can act on islet β cells, promote the transcription of insulin gene, insulin synthesis and secretion, stimulate the proliferation and differentiation of islet β cells, inhibit the apoptosis of islet β cells and increase the number of islet β cells.

In addition, GLP-1 can also act on islet α cells to strongly inhibit the release of glucagon, and act on islet δ cells to promote the secretion of somatostatin, and the somatostatin can also act as a paracrine hormone to participate in the inhibition of glucagon secretion.

Studies have shown that GLP-1 can significantly improve the blood glucose of animal models or patients with type 2 diabetes through various mechanisms, wherein, the effect of promoting the regeneration and repair of islet β cells and increasing the number of islet β cells is particularly significant.

2) Glucose Concentration-Dependent Hypoglycemic Effect

GLP-1 has a glucose concentration-dependent hypoglycemic effect, and only when the blood glucose level rises, GLP-1 exerts the hypoglycemic effect, and when the blood glucose level is normal, it will not further decrease.

3) Weight Loss

GLP-1 produces the effect of reducing body weight through various ways, including inhibiting gastrointestinal peristalsis and secretion of gastric juice, suppressing appetite and food intake, and delaying the emptying of gastric contents. GLP-1 can also act on the central nervous system (especially hypothalamus), so that the human body can have a sense of fullness and decreased appetite.

Novo Nordisk recently announced the phase III clinical results of semaglutide (a modified long-acting GLP-1 polypeptide), showing that in all randomized patients, after 68 weeks of treatment in obese patients, the mean baseline body weight of the semaglutide 2.4 mg treatment group decreased by 14.9% from 105.3 kg, and the body weight of the placebo group decreased by 2.4%; semalutide 2.4 mg group had 86.4% of patients with ≥5% weight loss and placebo group had 31.5% of patients with ≥5% weight loss.

Just because GLP-1 can significantly improve metabolic diseases by acting on GLP-1R receptor, many domestic and foreign companies have developed various modified or unmodified GLP-1 short-acting (three times a day) or long-acting (once a day or once a week) polypeptide drugs, which include: exenatide, liraglutide, albiglutide, dulaglutide, beinaglutide, lixisenatide, semaglutide, etc.

However, the clinical application of GLP-1 polypeptides and their modifications also faces many problems. Natural GLP-1 is easily degraded by dipeptidyl peptidase IV (DPP-IV) in the body, and its plasma half-life is less than 2 minutes. Continuous intravenous infusion or continuous subcutaneous injection is necessary to produce curative effect, which greatly limits the clinical application of GLP-1. Although the modified GLP-1 can prolong the half-life, its oral bioavailability is low, and there are still great challenges in oral administration. Therefore, there is an urgent need to develop small-molecule GLP-1R receptor agonist drugs that can be administered orally.

WO2018109607 discloses a compound with the following general formula and a candidate drug PF-06882961 and Ref-01 (compounds 4A-01 and 3A-01 in the original literature, which are used as reference compounds hereinafter).

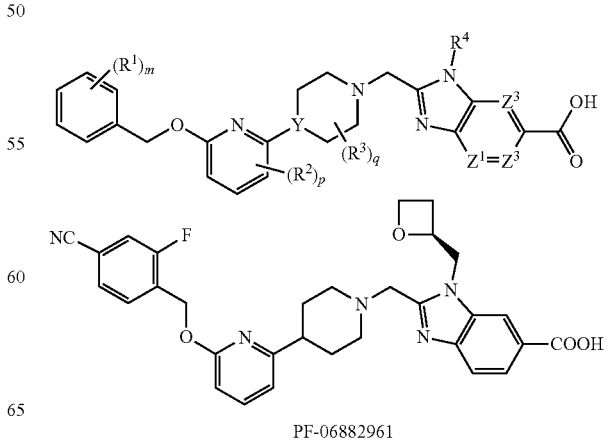

PF-06882961

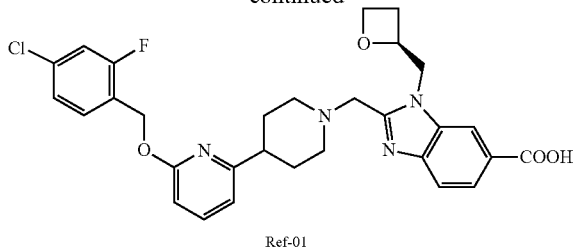

Ref-01

Surprisingly, compared with PF-06882961 and Ref-01, most of the compounds in the present disclosure not only show good activity, but also show better pharmacokinetic properties in vivo, and are more suitable for drug development.

WO2019239371 discloses the compound with the following general formula and the following compound Ref-02 (embodiment 1 in the original literature, which is used as a reference compound hereinafter).

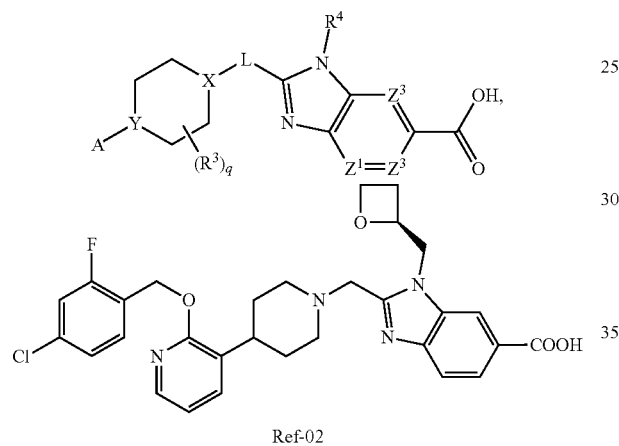

Ref-02

Surprisingly, compared with compound Ref-02, the compounds of the present disclosure not only have high activity, but also show better pharmacokinetic properties.

BRIEF SUMMARY OF THE INVENTION

The technical purpose of the present disclosure is to provide a class of compounds with GLP-1R receptor agonistic activity.

According to one aspect of the present disclosure, the present disclosure provides a compound represented by the following formula (I) or a pharmaceutically acceptable salt thereof, (I)

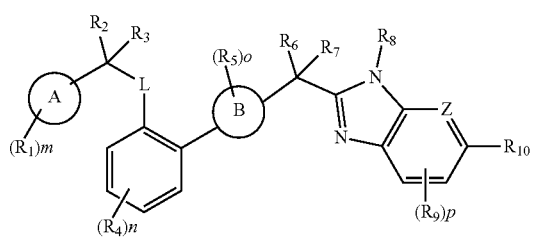

wherein,

A is phenyl or 5- to 6-membered heteroaryl containing one or two heteroatoms selected from O and N;

$R_1$ is —H, halogen, —CN, —OH, deuterium, —$C_{1-6}$ alkyl, —$C_{1-6}$ alkoxy, —$C_{2-6}$ alkenyl, —$C_{2-6}$ alkynyl, —$C_{6-10}$ aryl or —$C_{5-10}$ heteroaryl containing one or two heteroatoms selected from O and N; the —$C_{1-6}$ alkyl, —$C_{1-6}$ alkoxy, —$C_{2-6}$ alkenyl or —$C_{2-6}$ alkynyl is substituted by 0-3 F;

subscript m is an integer of 0, 1, 2 or 3;

$R_2$, $R_3$ are each independently —H, deuterium, or $C_{1-6}$ alkyl; or $R_2$, $R_3$ combining with the carbon atoms to which they are attached form a 3- to 6-membered cycloalkyl or heterocycloalkyl containing one or two heteroatoms selected from O and N;

L is —O—, —S—, —$NR_{11}$— or —$C(R_{11}R_{12})$—; the $R_{11}$, $R_{12}$ are hydrogen or —$C_{1-6}$ alkyl;

$R_4$ is halogen, —CN, —OH, deuterium, —$C_{1-6}$ alkyl, —$C_{1-6}$ alkoxy, —$C_{2-6}$ alkenyl or —$C_{2-6}$ alkynyl; the —$C_{1-6}$ alkyl, —$C_{1-6}$ alkoxy, —$C_{2-6}$ alkenyl or —$C_{2-6}$ alkynyl is substituted by 0-3 F;

subscript n is an integer of 0, 1 or 2;

B is

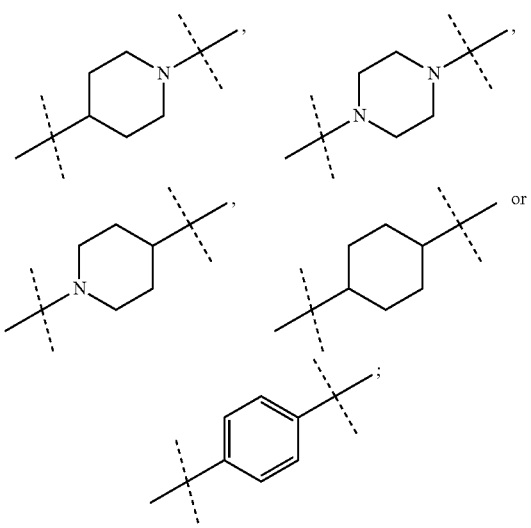

$R_5$ is —H, halogen, —CN, —OH, deuterium, —$C_{1-6}$ alkyl, —$C_{1-6}$ alkoxy, —$C_{2-6}$ alkenyl or —$C_{2-6}$ alkynyl; the —$C_{1-6}$ alkyl, —$C_{1-6}$ alkoxy, —$C_{2-6}$ alkenyl or —$C_{2-6}$ alkynyl is substituted by 0-3 F;

subscript o is an integer of 0, 1 or 2;

$R_6$, $R_7$ are each independently selected from —H, deuterium, or —$C_{1-6}$ alkyl; or $R_6$, $R_7$ combining with the carbon atoms to which they are attached form a 3- to 6-membered cycloalkyl or a 3- to 6-membered heterocycloalkyl containing one or two heteroatoms selected from O and N; or $R_6$, B ring combining with the carbon atoms to which they are attached form a 3- to 6-membered cycloalkyl or a 3- to 6-membered heterocycloalkyl containing one or two heteroatoms selected from O and N;

$R_8$ is —$C_{1-3}$ alkyl, -methylene-$C_{3-6}$ cycloalkyl or -methylene-$C_{4-6}$ heterocycloalkyl containing one or two heteroatoms selected from O and N; wherein, the —$C_{1-3}$ alkyl, -methylene-$C_{3-6}$cycloalkyl or -methylene-$C_{4-6}$ heterocycloalkyl containing one or two heteroatoms selected from O and N is unsubstituted or substituted by one or more substituents selected from halogen, —CN, —OH, deuterium, —$C_{1-6}$ alkyl, —$C_{1-6}$ alkoxy, —$C_{2-6}$ alkenyl, —$C_{2-6}$ alkynyl and 5- to 6-membered heteroaryl containing one or two heteroatoms selected from O and N;

Z is N or $CR_{13}$;

$R_9$ is hydrogen, halogen, —CN, —OH, deuterium, —$C_{1-6}$ alkyl, —$C_{1-6}$ alkoxy, —$C_{2-6}$ alkenyl or —$C_{2-6}$ alkynyl; the —$C_{1-6}$ alkyl, —$C_{1-6}$ alkoxy, —$C_{2-6}$ alkenyl or —$C_{2-6}$ alkynyl is substituted by 0-3 F;

subscript p is an integer of 0, 1 or 2;

$R_{10}$ is —COOH or an isostere of carboxyl;

$R_{13}$ is hydrogen, halogen, —CN, —OH, deuterium, —$C_{1-6}$ alkyl, —$C_{1-6}$ alkoxy, —$C_{2-6}$ alkenyl or —$C_{2-6}$ alkynyl; the —$C_{1-6}$ alkyl, —$C_{1-6}$ alkoxy, —$C_{2-6}$ alkenyl or —$C_{2-6}$ alkynyl is substituted by 0-3 F;

the halogen is selected from F, Cl and Br.

Preferably, the compound of the present disclosure has a structure represented by the following formula (II):

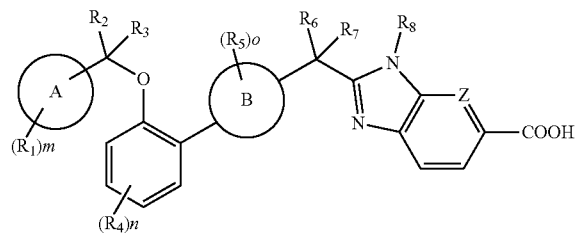

(II)

wherein,

A is phenyl or pyridyl;

$R_1$ is halogen, —CN, —OH, deuterium, —$C_{1-6}$ alkyl, —$C_{1-6}$ alkoxy, —$C_{2-6}$ alkenyl, or —$C_{2-6}$ alkynyl; the —$C_{1-6}$ alkyl, —$C_{1-6}$ alkoxy, —$C_{2-6}$ alkenyl, —$C_{2-6}$ alkynyl is substituted by 0-3 F;

subscript m is an integer of 0, 1 or 2;

$R_2$, $R_3$ are each independently —H, deuterium, or $C_{1-6}$ alkyl;

$R_4$ is halogen, —CN, —OH, deuterium, —$C_{1-6}$ alkyl or —$C_{1-6}$ alkoxy;

subscript n is an integer of 0 or 1;

B is

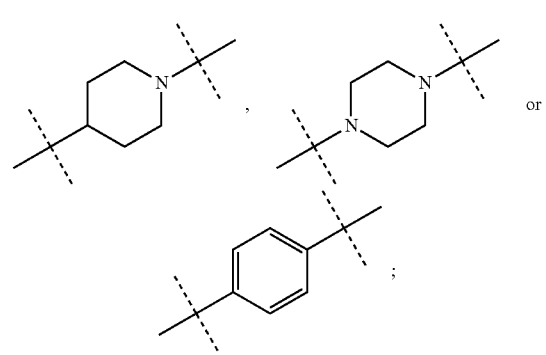

$R_5$ is halogen, —OH, —$C_{1-6}$ alkyl or —$C_{1-6}$ alkoxy;

subscript o is an integer of 0 or 1;

$R_6$, $R_7$ are each independently —H, deuterium, or $C_{1-6}$ alkyl; or $R_6$, $R_7$ combining with the carbon atoms to which they are attached form a 3- to 6-membered cycloalkyl or a 3- to 6-membered heterocycloalkyl containing one or two heteroatoms selected from O and N;

$R_8$ is —$C_{1-3}$ alkyl, -methylene-$C_{3-6}$ cycloalkyl or -methylene-$C_{4-6}$ heterocycloalkyl containing one or two heteroatoms selected from O and N; wherein, the —$C_{1-3}$ alkyl, -methylene-$C_{3-6}$ cycloalkyl or -methylene-$C_{4-6}$ heterocycloalkyl containing one or two heteroatoms selected from O and N is unsubstituted or substituted by one or more substituents selected from halogen, —CN, —OH, deuterium, —$C_{1-6}$ alkyl, —$C_{1-6}$ alkoxy, —$C_{2-6}$ alkenyl, —$C_{2-6}$ alkynyl and 5- to 6-membered heteroaryl containing one or two heteroatoms selected from O and N;

Z is N or $CR_{13}$;

$R_{13}$ is hydrogen, halogen, —CN, —OH, deuterium, —$C_{1-6}$ alkyl or —$C_{1-6}$ alkoxy.

Further preferably, the compound of the present disclosure has a structure represented by the following formula (III):

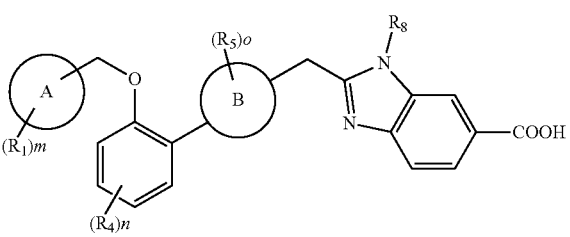

(III)

wherein, $R_1$ is halogen, —CN, —OH, deuterium, —$C_{1-6}$ alkyl, —$C_{1-6}$ alkoxy, —$C_{2-6}$ alkenyl, or —$C_{2-6}$ alkynyl; the —$C_{1-6}$ alkyl, —$C_{1-6}$ alkoxy, —$C_{2-6}$ alkenyl or —$C_{2-6}$ alkynyl is substituted by 0-3 F;

subscript m is an integer of 1 or 2;

A is phenyl, or pyridyl;

$R_4$ is halogen, —OH, deuterium, —$C_{1-6}$ alkyl or —$C_{1-6}$ alkoxy;

subscript n is an integer of 0 or 1;

B is

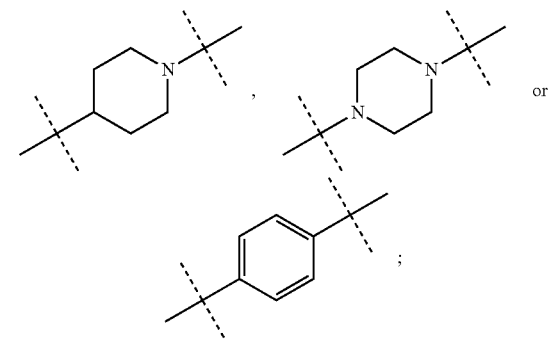

$R_5$ is halogen, —OH, —$C_{1-6}$ alkyl or —$C_{1-6}$ alkoxy;

subscript o is an integer of 0, 1 or 2;

$R_8$ is —$C_{1-3}$ alkyl, -methylene-$C_{3-6}$ cycloalkyl or -methylene-$C_{4-6}$ heterocycloalkyl.

Furthermore preferably, the compound of the present disclosure has a structure represented by the following formula (IV):

(IV)

wherein,
R₁ is halogen, —CN, —OH, deuterium, —$C_{1-6}$ alkyl, —$C_{1-6}$ alkoxy, —$C_{2-6}$ alkenyl, or —$C_{2-6}$ alkynyl; the —$C_{1-6}$ alkyl, —$C_{1-6}$ alkoxy, —$C_{2-6}$ alkenyl or —$C_{2-6}$ alkynyl is substituted by 0-3 F;
subscript m is an integer of 1 or 2;
A is phenyl, or pyridyl;
R₄ is halogen, —OH, deuterium, —$C_{1-6}$ alkyl or —$C_{1-6}$ alkoxy;
subscript n is an integer of 0 or 1;
B is or

;

R₅ is —$C_{1-6}$ alkyl;
subscript o is an integer of 0 or 1.

Furthermore preferably, in the structure of the compound represented by formula (IV) of the present disclosure, the R₁ is —F, —Cl, —Br, —CN, —$C_{1-6}$ alkyl, —$C_{1-6}$ alkoxy, —$C_{2-6}$ alkenyl or —$C_{2-6}$ alkynyl;
preferably, the m is 2;
preferably, the A is phenyl;
preferably, the R₄ is —F, or —Cl;
preferably, the B is Furthermore preferably, the subscript o is 0.
Furthermore preferably, the compound according to the present disclosure is selected from one of the following compounds:

1

2

3

4

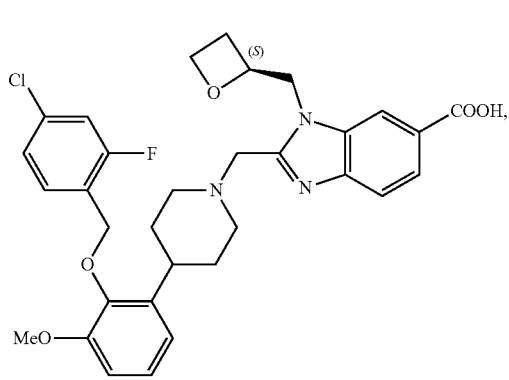
5
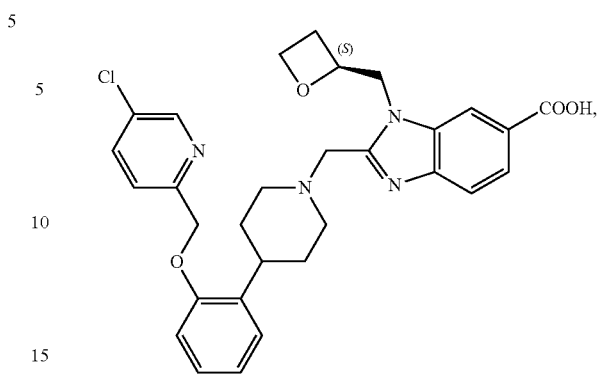
9
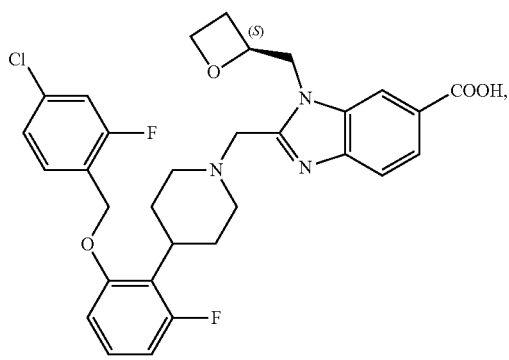
6
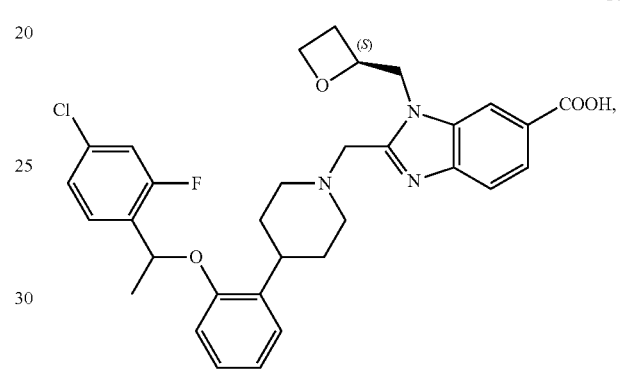
10
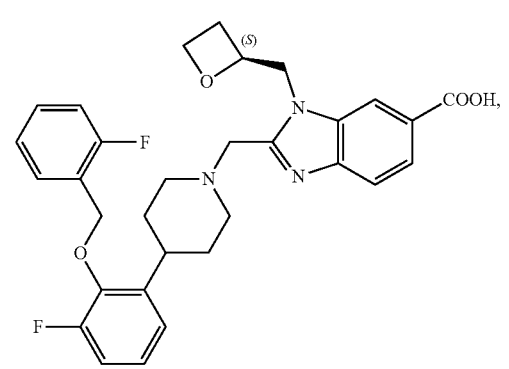
7
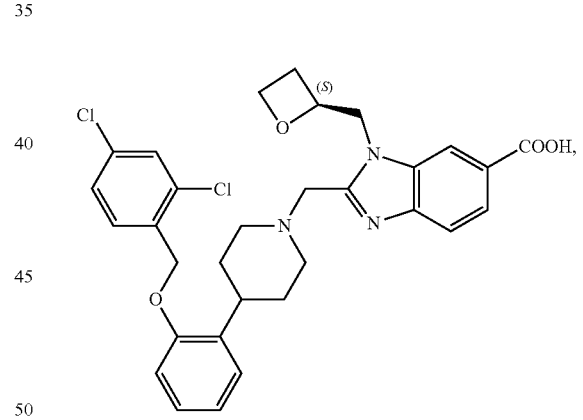
11
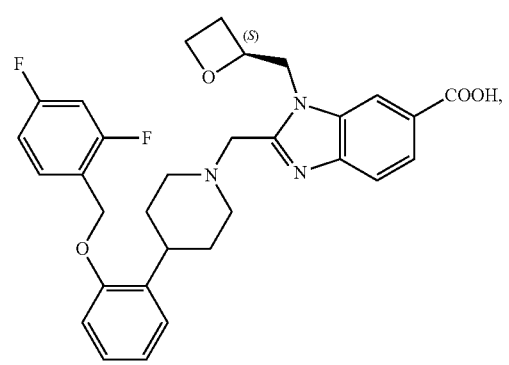
8
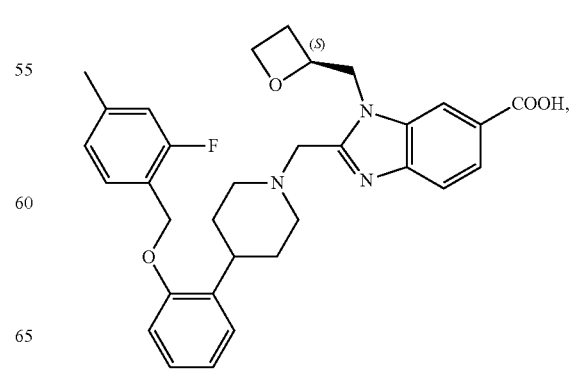
12

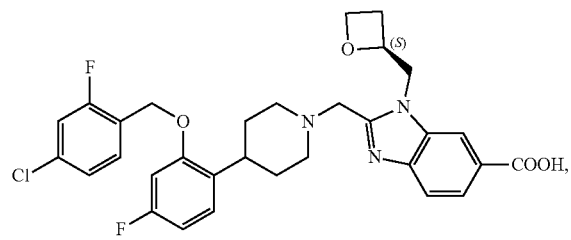
13
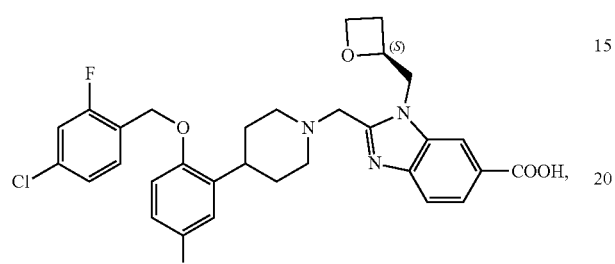
14
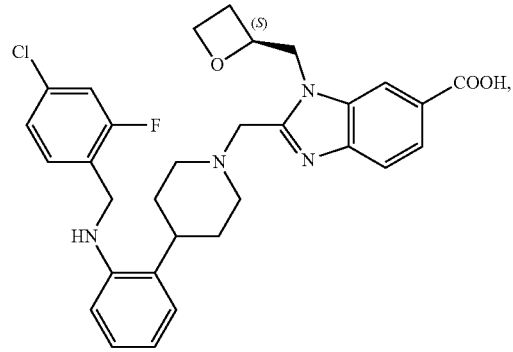
15
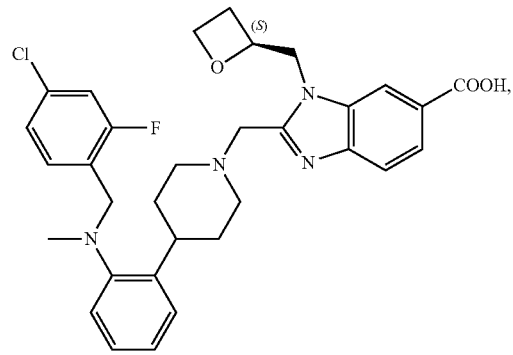
16
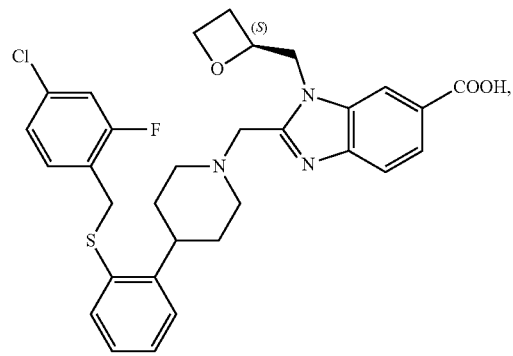
17
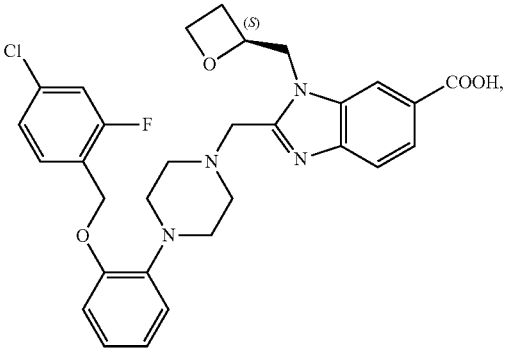
18
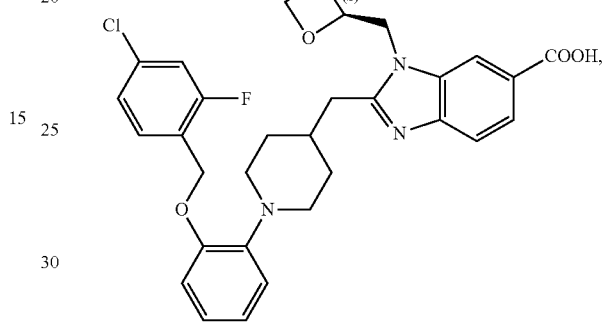
19
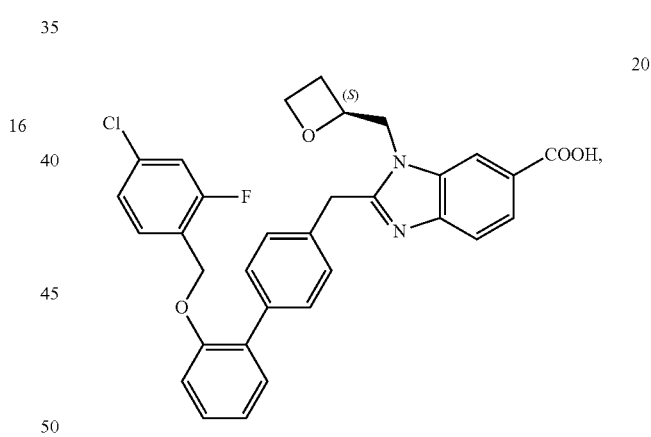
20
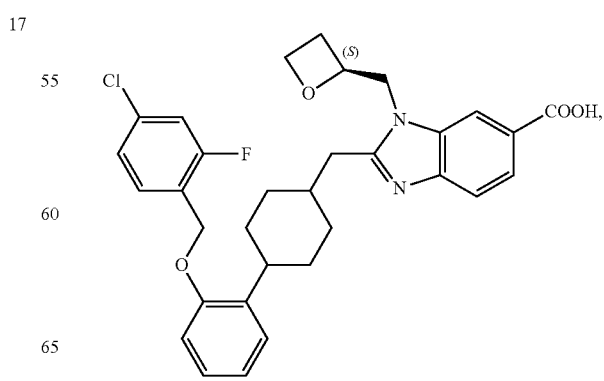
21

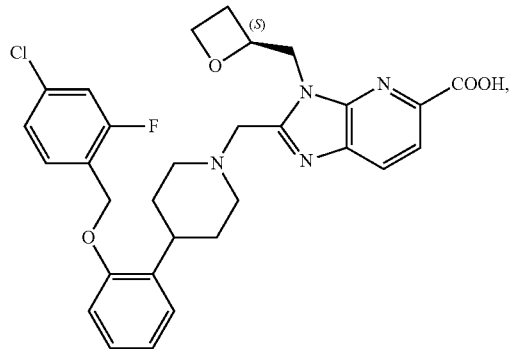
22
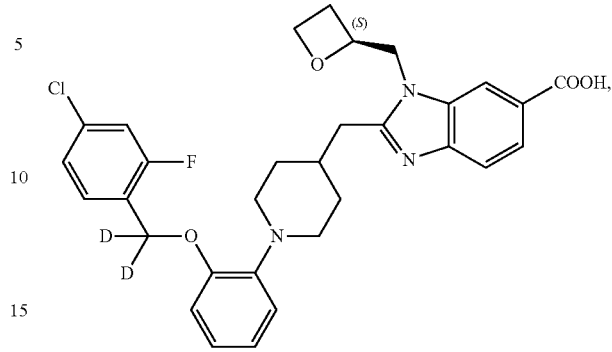
26
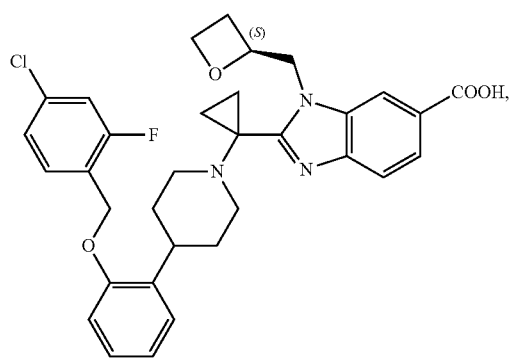
23
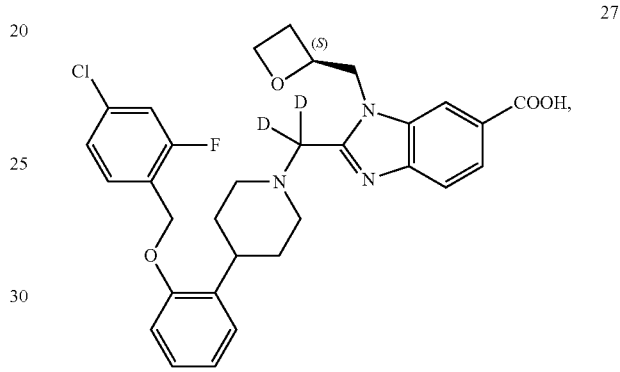
27
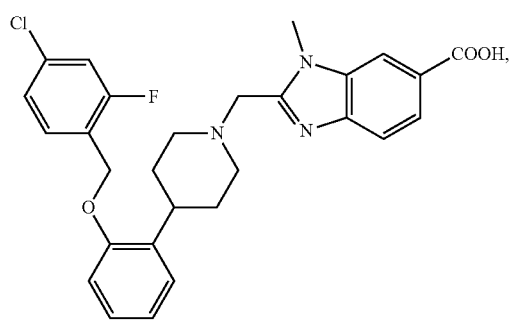
24
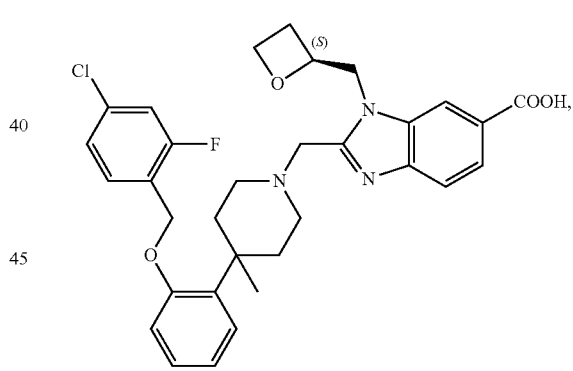
28
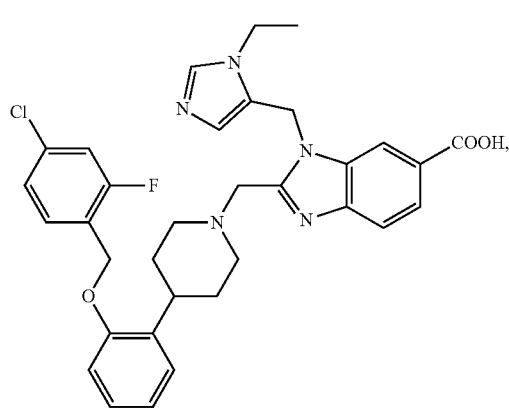
25
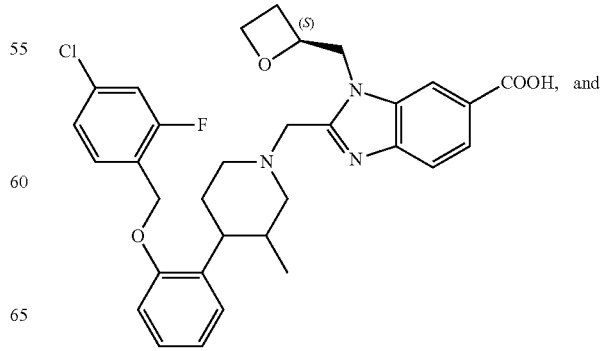
29, and -continued

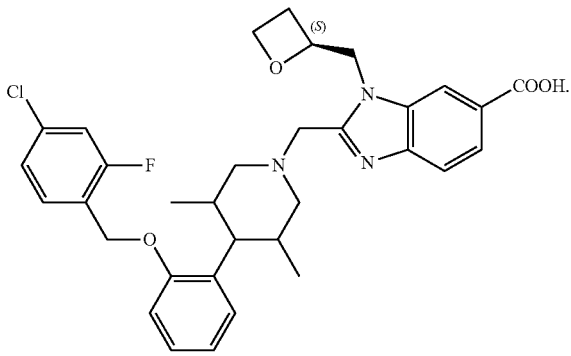

According to another aspect of the present disclosure, the present disclosure provides a pharmaceutical composition, comprising a therapeutically effective amount of the above compounds represented by formula (I) to formula (IV) or the pharmaceutically acceptable salt thereof as an active ingredient, and a pharmaceutically acceptable excipient.

According to another aspect of the present disclosure, the present disclosure provides a use of the above compound or the pharmaceutically acceptable salt thereof or the above pharmaceutical composition as an active ingredient in the manufacture of a medicament for treating metabolism-related diseases by activating a GLP-1R receptor.

In specific embodiments, the metabolism-related diseases are selected from any one of glucose intolerance, hyperglycemia, dyslipidemia, type 1 diabetes (T1D), type 2 diabetes (T2D), hypertriglyceridemia, syndrome X, insulin resistance, impaired glucose tolerance (IGT), diabetic dyslipidemia, hyperlipidemia, arteriosclerosis, atherosclerosis, hypertension, obesity, non-alcoholic fatty liver, non-alcoholic steatohepatitis, hepatic fibrosis, cirrhosis, lethargy, etc.

Beneficial Effects

The present disclosure synthesizes a novel class of GLP-1R receptor agonist compounds, which are confirmed by pharmacological experiments to have good agonistic activity on GLP-1R receptor, and therefore can be used for the treatment of GLP-1R receptor-related metabolic diseases. In addition, the compound of the present disclosure also exhibits excellent drug metabolism properties.

DETAILED DESCRIPTION OF THE INVENTION

Hereinafter, the present disclosure will be described in detail. Before proceeding with the description, it should be understood that the terms used in this specification and appended claims should not be construed as being limited to ordinary and dictionary meanings, but should be construed in accordance with the meaning and concept corresponding to the technical aspects of the present disclosure on the basis of the principle that allows the inventors to appropriately define the terms for optimum interpretation. Therefore, the description set forth herein is merely a preferred example for the purpose of illustration and is not intended to limit the scope of the present disclosure, and it should be understood that other equivalents or modifications may be made thereto without departing from the spirit and scope of the present disclosure.

According to the present disclosure, all terms cited herein have the same meanings as understood by those skilled in the art, unless otherwise stated.

As used herein, the term "salt" refers to compounds containing cations and anions that can be produced by protonation of proton-acceptable sites and/or deprotonation of proton-available sites. It is worth noting that protonation of the proton-acceptable site leads to the formation of cationic substances whose charge is balanced by the presence of physiological anions, while deprotonation of the proton-available site leads to the formation of anionic substances whose charge is balanced by the presence of physiological cations.

The term "pharmaceutically acceptable salt" means that the salt is pharmaceutically acceptable. Examples of pharmaceutically acceptable salts include, but are not limited to: (1) acid addition salts, formed with inorganic acids, such as hydrochloric acid, hydrobromic acid, sulfuric acid, nitric acid, phosphoric acid, etc.; or formed with organic acids, such as glycolic acid, pyruvic acid, lactic acid, malonic acid, malic acid, maleic acid, fumaric acid, tartaric acid, citric acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, p-toluenesulfonic acid, camphoric acid, dodecylsulfuric acid, gluconic acid, glutamic acid, salicylic acid, cis-muconic acid, etc.; or (2) base addition salts, formed with any one of the conjugate bases of the above inorganic acids, wherein the conjugate base includes a cation component selected from $Na^+$, $K^+$, $Mg^{2+}$, $Ca^{2+}$, $NH_xR_{4-x}^+$, wherein $NH_xR_{4-x}^+$ (R is $C_{1-4}$ alkyl, and subscript x is an integer selected from 0, 1, 2, 3 or 4) represents the cation in the quaternary ammonium salt. It should be understood that all salts involving pharmaceutically acceptable salts include solvent addition form (solvate) or crystalline form (polymorph) as defined herein for the same acid addition salts.

The term "$C_{1-M}$ alkyl" refers to an alkyl containing 1-M carbon atoms, for example, wherein M is an integer having the following values: 2, 3, 4, 5, 6, 7, 8, 9, 10, 11, 12, 13, 14, 15, 16, 17, 18, 19, 20, 21, 22, 23, 24, 25, 26, 27, 28, 29 or 30. For example, the term "$C_{1-6}$ alkyl" refers to an alkyl containing 1-6 carbon atoms. Examples of alkyl include, but are not limited to, lower alkyl including methyl, ethyl, propyl, isopropyl, n-butyl, isobutyl, tert-butyl, pentyl, isopentyl, neopentyl, hexyl, heptyl and octyl.

The term "$C_{3-M}$ cycloalkyl" refers to a cycloalkyl containing 3-M carbon atoms, for example, wherein M is an integer with the following values: 4, 5, 6, 7, 8. For example, the term "$C_{3-6}$ cycloalkyl" refers to a cycloalkyl containing 3-6 carbon atoms. Examples of cycloalkyl include, but are not limited to, cyclopropyl, cyclobutyl, cyclopentyl, cyclohexyl, etc.

The term "aryl" refers to an aromatic system, which may be a single ring or polyaromatic rings that are fused or linked together such that at least a portion of the fused or linked rings form a conjugated aromatic system. Aryl groups include, but are not limited to: phenyl, naphthyl, tetrahydronaphthyl. Aryl may be optionally substituted, such as aryl or heterocycle that may be substituted by 1-4 groups selected from the group consisting of halogen, —CN, —OH, —NO₂, amino, alkyl, cycloalkyl, alkenyl, alkynyl, alkoxy, aryloxy, substituted alkoxy, alkylcarbonyl, alkylcarboxy, alkylamino, or arylthio.

The term "substituted" means that the reference group may be substituted by one or more additional groups, and the additional groups are individually and independently selected from alkyl, cycloalkyl, aryl, heteroaryl, heteroalicyclic hydrocarbon, hydroxy, alkoxy, alkylthio, arylthio, alkylsulfinyl, arylsulfinyl, alkylsulfonyl, arylsulfonyl, cyano, halogen, carbonyl, thiocarbonyl, nitro, haloalkyl, fluoroalkyl and amino, including monosubstituted and disubstituted amino groups and protected derivatives thereof.

The compound represented by formula (I) or the pharmaceutically acceptable salt thereof and the pharmaceutical composition comprising the compound provided by the present disclosure may be in various forms, such as tablets, capsules, powders, syrups, solution forms, suspensions and aerosols, and may be present in a suitable solid or liquid carrier or diluent and in a suitable sterile apparatus for injection or infusion.

Various dosage forms of the pharmaceutical composition of the present disclosure can be prepared according to conventional preparation methods in the field of pharmacy. For example, the unit dose of the formulation contains 0.05-200 mg of the compound represented by formula (I) or the pharmaceutically acceptable salt thereof, preferably, the unit dose of the formulation contains 0.1 mg-100 mg of the compound represented by formula (I).

The compound represented by formula (I) and the pharmaceutical composition of the present disclosure can be clinically used in mammals, including humans and animals, and can be administered via oral, nasal, dermal, pulmonary or gastrointestinal routes. Oral administration is most preferred. The optimal daily dose is 0.01-200 mg/kg body weight in a single dose or 0.01-100 mg/kg body weight in divided doses. Regardless of the method of administration, the optimal dose for an individual should depend on the specific treatment. It is common to start with a small dose and gradually increase the dose until the most suitable dose is found.

In the present disclosure, the term "effective amount" may refer to an effective amount of the dose and time period required to achieve the desired effect. The effective amount may vary depending on certain factors, such as the type of disease or condition of the disease at the time of treatment, the configuration of the particular subject organ being administered, the size of the individual patient or the severity of the disease or symptom. The effective amount of a particular compound can be determined empirically by those skilled in the art without excessive experiments.

A typical formulation is prepared by mixing the compound represented by formula (I) of the present disclosure and a carrier, diluent or excipient. Suitable carrier, diluent or excipient is well known to those skilled in the art and includes substances such as carbohydrates, waxes, water-soluble and/or swellable polymers, hydrophilic or hydrophobic substances, gelatin, oils, solvents, water, etc.

The particular carrier, diluent or excipient employed will depend upon the mode and purpose of use of the compound of the present disclosure. Solvents are generally selected on the basis of solvents considered safe and effective for administration to mammals by those skilled in the art. In general, safe solvents are non-toxic aqueous solvents such as water, and other non-toxic solvents that are soluble or miscible in water. Suitable aqueous solvents include one or more of water, ethanol, propylene glycol, polyethylene glycol (e.g., PEG400, PEG300), etc. The formulation may also include one or more buffers, stabilizers, surfactants, wetting agents, lubricants, emulsifiers, suspensions, preservatives, antioxidants, opacifiers, glidants, processing aids, colorants, sweeteners, spices, flavorings or other known additives to enable the drug to be manufactured or used in an acceptable form.

When the compound represented by formula (I) of the present disclosure is used in combination with at least one other drug, the two or more drugs can be used separately or in combination, preferably in the form of a pharmaceutical composition. The compound represented by formula (I) or the pharmaceutical composition of the present disclosure can be administered separately or in combination in any known form of oral administration, intravenous injection, rectal administration, vaginal administration, transdermal absorption, other local or systemic administration form to the subject.

The pharmaceutical composition may also include one or more buffers, stabilizers, surfactants, wetting agents, lubricants, emulsifiers, suspensions, preservatives, antioxidants, opacifiers, glidants, processing aids, colorants, sweeteners, spices, flavorings or other known additives to enable the pharmaceutical composition to be manufactured or used in an acceptable form.

The drug of the present disclosure is preferably administered orally. Solid dosage forms for oral administration may include capsules, tablets, powder or granule formulations. In solid dosage forms, the compound or the pharmaceutical composition of the present disclosure is mixed with at least one inert excipient, diluent or carrier. Suitable excipients, diluents or carriers include substances such as sodium citrate or dicalcium phosphate, or starch, lactose, sucrose, mannitol, silicic acid, etc.; binders such as carboxymethylcellulose, alginate, gelatin, polyvinylpyrrolidone, sucrose, gum arabic, etc.; wetting agents such as glycerin, etc.; disintegrants such as agar, calcium carbonate, potato or tapioca starch, alginic acid, specific complex silicate, sodium carbonate, etc.; solution blockers such as paraffin, etc.; absorption promoters such as quaternary ammonium compounds, etc.; adsorbents such as kaolin, bentonite, etc.; lubricants such as talc, calcium stearate, magnesium stearate, solid polyethylene glycol, sodium dodecyl sulfate, etc. In the case of capsules and tablets, the dosage form may also include a buffer. Similar types of solid compositions may also be used as fillers in soft and hard filled gelatin capsules, using lactose and high molecular weight polyethylene glycols as excipients.

Liquid dosage forms for oral administration include pharmaceutically acceptable emulsions, solutions, suspensions, syrups and elixirs. In addition to the compound or the pharmaceutical composition thereof of the present disclosure, the liquid dosage form may contain inert diluents commonly used in the art, such as water or other solvents; solubilizers and emulsifiers such as ethanol, isopropyl alcohol, ethyl carbonate, ethyl acetate, benzyl alcohol, benzyl benzoate, propylene glycol, 1,3-butanediol, dimethyl formamide; oils (e.g., cottonseed oil, groundnut oil, corn germ oil, olive oil, castor oil, sesame oil); glycerin; tetrahydrofurfuryl alcohol; fatty acid esters of polyethylene glycol and dehydrated sorbitol; or mixtures of several of these substances, etc.

In addition to these inert diluents, the composition may also include excipients, such as one or more of wetting agents, emulsifiers, suspensions, sweeteners, flavorings and spices.

In the case of suspensions, in addition to the compound represented by general formula (I) or the pharmaceutically acceptable salt thereof or the pharmaceutical composition containing the same of the present disclosure, suspensions may further contain carriers such as suspending agents such as ethoxylated isostearyl alcohol, polyoxyethylene sorbitol, dehydrated sorbitol ester, microcrystalline cellulose, AlO(OH), bentonite, agar and tragacanth gum, or mixtures of several of these substances, etc.

The compound represented by formula (I) or the pharmaceutically acceptable salt thereof or the pharmaceutical composition containing the same of the present disclosure may be administered in other topical delivery forms, including creams, powders, sprays and inhalants. The drug may be mixed under sterile conditions with a pharmaceutically acceptable excipient, diluent or carrier and any one preservative, buffer or propellant as desired. Ophthalmic formulations, ophthalmic ointments, powders and solutions are also intended to be within the scope of the present disclosure.

In addition, the present disclosure also covers kits (such as pharmaceutical packaging). Provided kits may contain the pharmaceutical composition or the compound described herein and a container (e.g., vial, ampoule, bottle, syringe and/or sub-package or other suitable container). In some embodiments, provided kits may optionally further contain a second container, comprising a pharmaceutically acceptable excipient for diluting or suspending the pharmaceutical composition or the compound described herein. In some embodiments, the pharmaceutical compositions or the compounds described herein disposed in a first container and a second container are combined to form a unit dosage form.

In some embodiments, the kits described herein further contain instructions for using the compound or the pharmaceutical composition contained in the kit. The kits described herein may also include information required by regulatory agencies, such as the U.S. Food and Drug Administration (FDA). In some embodiments, the information contained in the kit is prescription information. In some embodiments, the kits and instructions are provided for use in treating a proliferative disease in a subject in need thereof and/or preventing a proliferative disease in a subject in need thereof. The kits described herein may contain one or more additional pharmaceutical agents as separate compositions.

The present disclosure is described in further detail hereinafter in connection with specific embodiments, but the present disclosure is not limited to the following embodiments, and embodiments are intended to better illustrate certain specific implementations of the present disclosure and are not to be construed as limiting the scope of the present disclosure in any way. The conditions not indicated in the embodiments are conventional conditions. Unless otherwise specified, the reagents and instruments used in the following embodiments are all commercially available products.

The structures of the compounds in the following embodiments are determined by nuclear magnetic resonance (NMR) or/and mass spectrometry (MS). NMR shifts (δ) are given in units of $10^{-6}$ (ppm). The determination of NMR uses a Bruker AVANCE-400 nuclear magnetic instrument, and the determination solvent is deuterated dimethyl sulfoxide (DMSO-$d_6$), deuterated chloroform (CDCl$_3$), deuterated methanol (CD$_3$OD), and the internal standard is tetramethylsilane (TMS).

The determination of MS uses a FINNIGAN LCQAd (ESI) mass spectrometer (manufacturer: Thermo, model: Finnigan LCQ advantage MAX).

Column chromatography generally uses Yantai Huanghai silica gel 200-300 mesh silica gel as a carrier.

The temperature of the reaction in the embodiment is room temperature, 20° C.-30° C., unless otherwise specified.

The elution system of the column chromatography adopted in the embodiment includes: A: dichloromethane and methanol system, B: n-hexane and ethyl acetate system, C: petroleum ether and ethyl acetate system, D: acetone and petroleum ether system, and the volume ratio of the solvent is adjusted according to the polarity of the compound.

Abbreviations used in experiments: D: deuterium; h: hour; min: minute; EA: ethyl acetate; DMF: N,N-dimethylformamide; mL: milliliter; mmol: millimole; Cs$_2$CO$_3$: cesium carbonate; PdCl$_2$(dtbpf): [1,1'-bis(diphenylphosphino)ferrocene]palladium dichloride; Boc: tert-butoxycarbonyl; THF: tetrahydrofuran; DCM: dichloromethane; DIPEA: diisopropylethylamine; TFA: trifluoroacetic acid; TEA: triethylamine; THF: tetrahydrofuran; TBD: 1,5,7-triazabicyclo[4.4.0]dec-5-ene; N: moles per liter.

Embodiment 1: Preparation of Compound 1

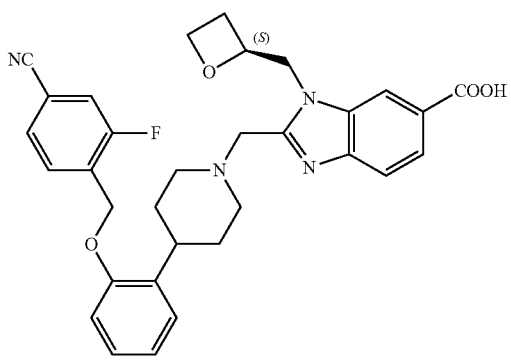

Compound 1 was prepared using starting material 1-1 according to the following route.

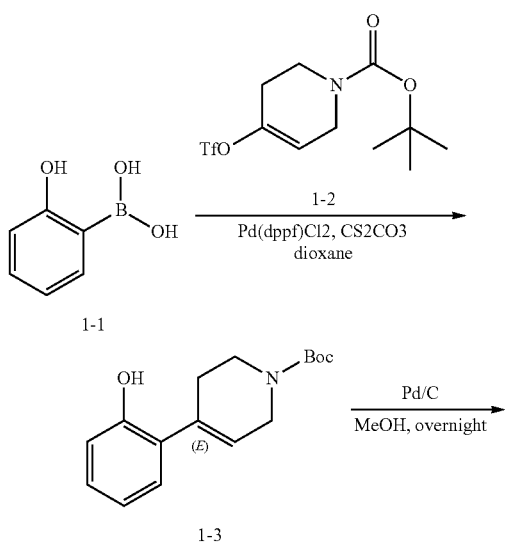

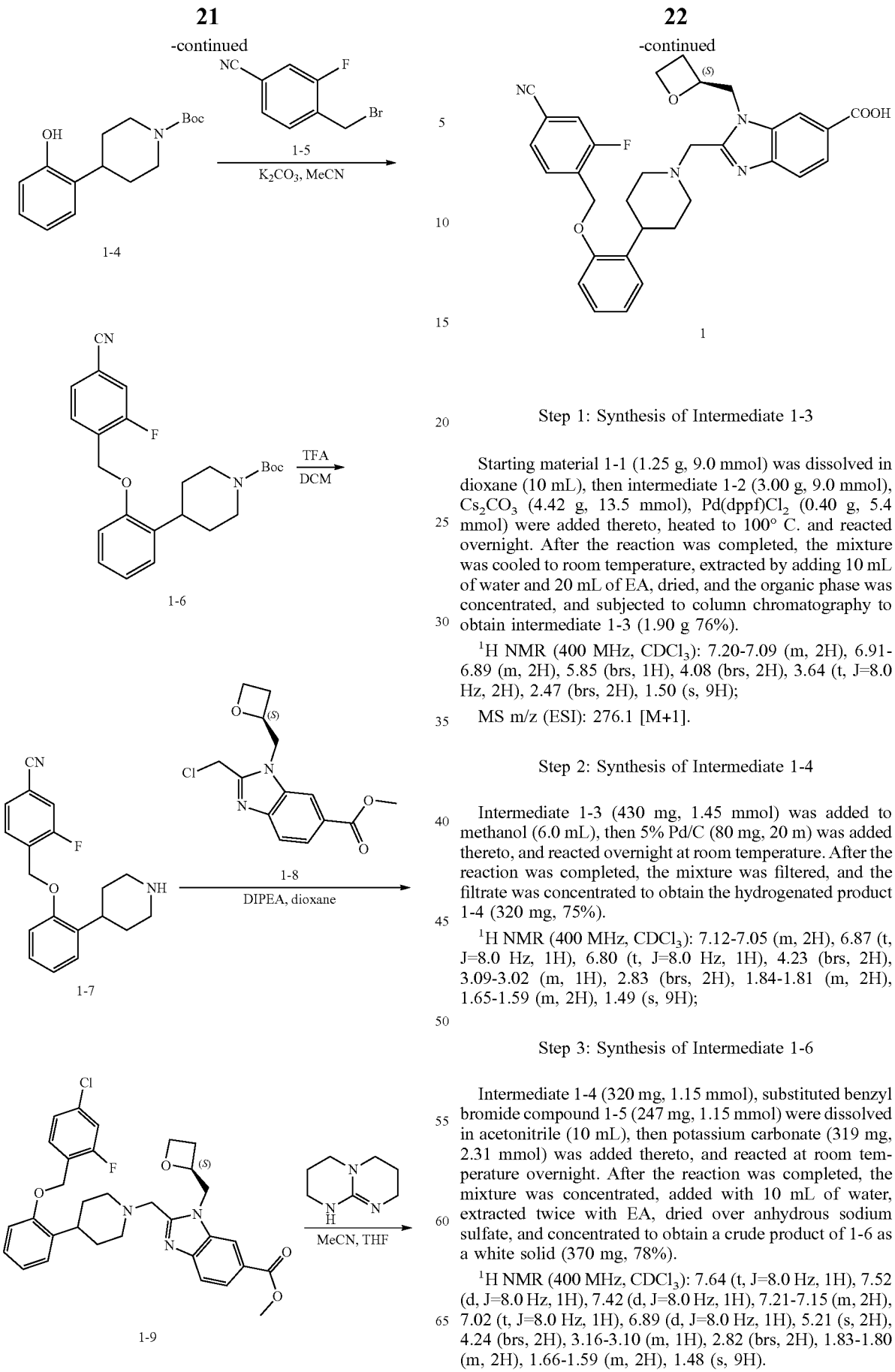

Step 1: Synthesis of Intermediate 1-3

Starting material 1-1 (1.25 g, 9.0 mmol) was dissolved in dioxane (10 mL), then intermediate 1-2 (3.00 g, 9.0 mmol), Cs$_2$CO$_3$ (4.42 g, 13.5 mmol), Pd(dppf)Cl$_2$ (0.40 g, 5.4 mmol) were added thereto, heated to 100° C. and reacted overnight. After the reaction was completed, the mixture was cooled to room temperature, extracted by adding 10 mL of water and 20 mL of EA, dried, and the organic phase was concentrated, and subjected to column chromatography to obtain intermediate 1-3 (1.90 g 76%).

$^1$H NMR (400 MHz, CDCl$_3$): 7.20-7.09 (m, 2H), 6.91-6.89 (m, 2H), 5.85 (brs, 1H), 4.08 (brs, 2H), 3.64 (t, J=8.0 Hz, 2H), 2.47 (brs, 2H), 1.50 (s, 9H);

MS m/z (ESI): 276.1 [M+1].

Step 2: Synthesis of Intermediate 1-4

Intermediate 1-3 (430 mg, 1.45 mmol) was added to methanol (6.0 mL), then 5% Pd/C (80 mg, 20 m) was added thereto, and reacted overnight at room temperature. After the reaction was completed, the mixture was filtered, and the filtrate was concentrated to obtain the hydrogenated product 1-4 (320 mg, 75%).

$^1$H NMR (400 MHz, CDCl$_3$): 7.12-7.05 (m, 2H), 6.87 (t, J=8.0 Hz, 1H), 6.80 (t, J=8.0 Hz, 1H), 4.23 (brs, 2H), 3.09-3.02 (m, 1H), 2.83 (brs, 2H), 1.84-1.81 (m, 2H), 1.65-1.59 (m, 2H), 1.49 (s, 9H);

Step 3: Synthesis of Intermediate 1-6

Intermediate 1-4 (320 mg, 1.15 mmol), substituted benzyl bromide compound 1-5 (247 mg, 1.15 mmol) were dissolved in acetonitrile (10 mL), then potassium carbonate (319 mg, 2.31 mmol) was added thereto, and reacted at room temperature overnight. After the reaction was completed, the mixture was concentrated, added with 10 mL of water, extracted twice with EA, dried over anhydrous sodium sulfate, and concentrated to obtain a crude product of 1-6 as a white solid (370 mg, 78%).

$^1$H NMR (400 MHz, CDCl$_3$): 7.64 (t, J=8.0 Hz, 1H), 7.52 (d, J=8.0 Hz, 1H), 7.42 (d, J=8.0 Hz, 1H), 7.21-7.15 (m, 2H), 7.02 (t, J=8.0 Hz, 1H), 6.89 (d, J=8.0 Hz, 1H), 5.21 (s, 2H), 4.24 (brs, 2H), 3.16-3.10 (m, 1H), 2.82 (brs, 2H), 1.83-1.80 (m, 2H), 1.66-1.59 (m, 2H), 1.48 (s, 9H).

Step 4: Synthesis of Intermediate 1-7

Intermediate 1-6 (350 mg, 0.85 mmol) was added to DCM (20 mL), then TFA (2.0 mL) was added thereto, and reacted at room temperature for 2.0 hours. After the reaction was completed, the mixture was concentrated, added with EA, and the pH was adjusted to 8 with saturated sodium bicarbonate aqueous solution. The phases were separated, and the organic phase was dried and concentrated to obtain intermediate 1-8 (270 mg), which was directly put into the next reaction without purification.

Step 5: Synthesis of Intermediate 1-9

Intermediate 1-7 (270 mg, 0.87 mmol), chlorinated compound 1-8 (205 mg, 0.69 mmol, synthesized with reference to WO2018109607) were dissolved in dioxane (6 mL), and DIPEA (393 mg, 3.0 mmol) was added thereto, heated to 50° C. and reacted. After the reaction was completed, $H_2O$ (5 mL) and EA (15 mL) were added for extraction, and the organic phase was dried and concentrated, and purified by column chromatography to obtain intermediate 1-9 (200 mg, 40%).

$^1$H NMR (400 MHz, CDCl$_3$): 8.18 (s, 1H), 7.98 (d, J=8.0 Hz, 1H), 7.77 (d, J=8.0 Hz, 1H), 7.65 (t, J=8.0 Hz, 1H), 7.54 (d, J=8.0 Hz, 1H), 7.42 (d, J=8.0 Hz, 1H), 7.24-7.16 (m, 2H), 7.01 (t, J=8.0 Hz, 1H), 6.89 (d, J=8.0 Hz, 1H), 5.26-5.23 (m, 1H), 5.20 (s, 2H), 4.76-4.61 (m, 3H), 4.44-4.40 (m, 1H), 4.00 (s, 2H), 3.95 (s, 3H), 3.07-2.98 (m, 3H), 2.77-2.75 (m, 1H), 2.50-2.45 (m, 1H), 2.35-2.28 (m, 2H), 1.85-1.83 (m, 2H), 1.76-1.71 (m, 2H).

MS m/z (ESI): 569.2 [M+1].

Step 6: Synthesis of Compound 1

Intermediate 1-9 (100 mg, 0.17 mmol) was added to a mixed solvent of MeCN/THF (4 mL/4 mL), then 0.97 N 1,5,7-triazabicyclo[4.4.0]dec-5-ene (TBD) (0.4 mL) was added thereto, and the reaction was carried out overnight at room temperature. Additional 0.97N TBD (1.0 mL) was added thereto, and the reaction was continued for 2 hours. The mixture was concentrated to remove the solvent, added with water (6.0 mL). The pH of the system was adjusted to 5-6 with 1N citric acid aqueous solution, and the mixture was added with EA (10 mL), extracted to obtain the organic phase, dried and concentrated, purified by column chromatography to obtain compound 1 (70 mg, 72%).

$^1$H NMR (400 MHz, DMSO-d$_6$): 12.74 (brs, 1H), 8.28 (s, 1H), 7.96 (d, J=8.0 Hz, 1H), 7.80-7.74 (m, 3H), 7.65 (t, J=8.0 Hz, 1H), 7.22 (t, J=8.0 Hz, 2H), 7.08 (d, J=8.0 Hz, 1H), 6.97 (d, J=8.0 Hz, 1H), 5.25 (s, 2H), 5.10 (s, 1H), 4.82-4.79 (m, 1H), 4.69-4.65 (m, 1H), 4.51-4.48 (m, 1H), 4.39-4.36 (m, 1H), 4.04-3.94 (m, 1H), 3.82-3.79 (m, 1H), 3.01-2.89 (m, 3H), 2.70-2.68 (m, 1H), 2.45-2.43 (m, 1H), 2.24-2.18 (m, 2H), 1.70-1.60 (m, 4H).

MS m/z (ESI): 555.1 [M+1].

Embodiment 2: Preparation of Compound 2

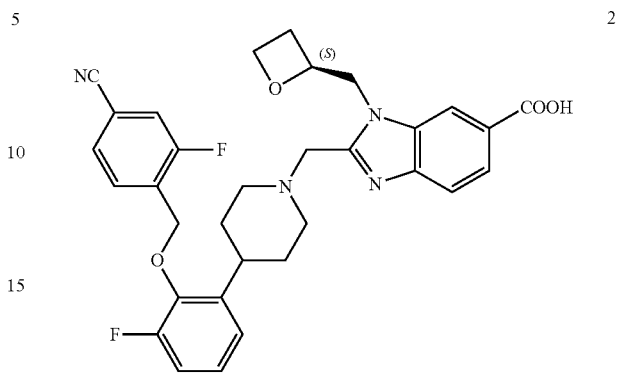

According to the similar synthesis method of embodiment 1, the starting material (3-fluoro-2-hydroxyphenyl)phenylboronic acid was replaced with 1-1 (2-hydroxyphenyl) to prepare compound 2.

$^1$H NMR (400 MHz, DMSO-d$_6$): 8.19 (s, 1H), 7.84 (d, J=8.0 Hz, 1H), 7.74-7.66 (m, 3H), 7.58 (d, J=8.0 Hz, 1H), 7.06-6.96 (m, 3H), 5.08 (s, 2H), 5.01-4.99 (m, 1H), 4.74-4.68 (m, 1H), 4.58-4.55 (m, 1H), 4.42-4.40 (m, 1H), 4.29-4.27 (m, 1H), 3.87 (d, J=16.0 Hz, 1H), 3.72 (d, J=16.0 Hz, 1H), 2.90-2.87 (m, 1H), 2.76-2.63 (m, 3H), 2.35-2.30 (m, 1H), 2.04-1.91 (m, 2H), 1.51-1.39 (m, 4H).

MS m/z (ESI): 573.1 [M+1].

Embodiment 3: Preparation of Compound 3

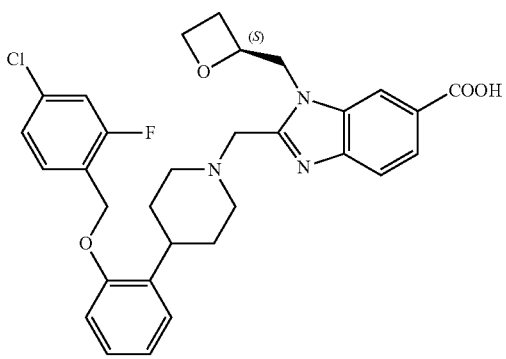

According to the similar synthetic method of embodiment 1, except adopting 1-(bromomethyl)-4-chloro-2-fluorobenzene in step 3 of embodiment 1 instead of compound 1-5 (4-(bromomethyl)-3-fluorobenzonitrile), compound 3 was prepared in the same method as in embodiment 1.

$^1$H NMR (400 MHz, DMSO-d$_6$): 8.19 (s, 1H), 7.74 (d, J=8.0 Hz, 1H), 7.58 (d, J=8.0 Hz, 1H), 7.51-7.47 (m, 2H), 7.44 (d, J=8.0 Hz, 1H), 7.11-7.08 (m, 2H), 7.01 (d, J=8.0 Hz, 1H), 6.87-6.84 (m, 1H), 5.06 (s, 2H), 5.01-4.99 (m, 1H), 4.74-4.70 (m, 1H), 4.58-4.55 (m, 1H), 4.42-4.40 (m, 1H), 4.29-4.27 (m, 1H), 3.87-3.75 (m, 2H), 2.95-2.92 (m, 1H), 2.79-2.70 (m, 2H), 2.68-2.64 (m, 1H), 2.35-2.31 (m, 1H), 2.11-2.00 (m, 2H), 1.60-1.55 (m, 4H).

MS m/z (ESI): 564.2 [M+1].

Embodiment 4: Preparation of Compound 4

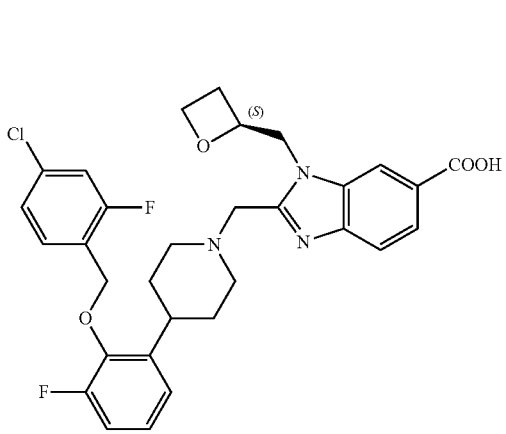

According to the similar synthesis method of embodiments 1 and 3, the starting material (3-fluoro-2-hydroxyphenyl)phenylboronic acid was replaced with 1-1 (2-hydroxyphenyl) to prepare compound 4.

$^1$H NMR (400 MHz, DMSO-d$_6$): 12.74 (brs, 1H), 8.28 (s, 1H), 7.82 (d, J=8.0 Hz, 1H), 7.67 (d, J=8.0 Hz, 1H), 7.54-7.52 (m, 2H), 7.36 (d, J=8.0 Hz, 1H), 7.13-7.04 (m, 3H), 5.08 (s, 2H), 4.83-4.77 (m, 1H), 4.67-4.64 (m, 1H), 4.51-4.49 (m, 1H), 4.38-4.36 (m, 1H), 4.04-3.92 (m, 2H), 3.80-3.77 (m, 1H), 2.95-2.90 (m, 1H), 2.84-2.73 (m, 3H), 2.43-2.40 (m, 1H), 2.09-2.00 (m, 2H), 1.58-1.41 (m, 4H).

MS m/z (ESI): 582.0 [M+1].

Embodiment 5: Preparation of Compound 5

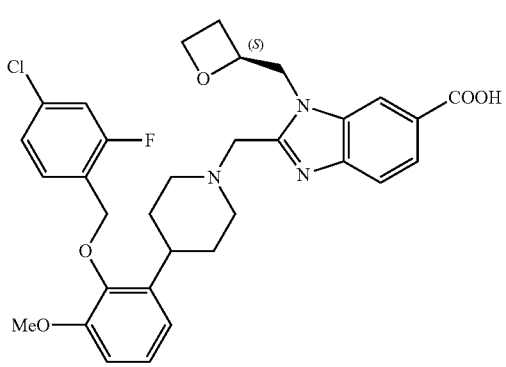

According to the similar synthesis method of embodiments 1 and 3, the starting material (2-hydroxy-3-methoxyphenyl)phenylboronic acid was replaced with 1-1 (2-hydroxyphenyl) to prepare compound 5.

MS m/z (ESI): 594.1 [M+1].

Embodiment 6: Preparation of Compound 6

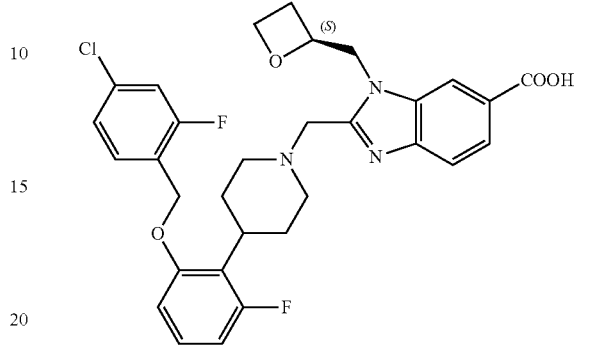

According to the similar synthesis method of embodiments 1 and 3, the starting material (2-hydroxy-3-methoxyphenyl)phenylboronic acid was replaced with 1-1 (2-hydroxyphenyl) to prepare compound 6.

$^1$H NMR (400 MHz, DMSO-d$_6$): 12.71 (brs, 1H), 8.27 (s, 1H), 7.81 (d, J=8.0 Hz, 1H), 7.79-7.54 (m, 3H), 7.38 (d, J=8.0 Hz, 1H), 7.23-7.21 (m, 1H), 6.98 (d, J=8.0 Hz, 1H), 6.77 (d, J=8.0 Hz, 1H), 5.17 (s, 2H), 5.10-5.05 (m, 1H), 4.77-4.71 (m, 1H), 4.62-4.58 (m, 1H), 4.49-4.45 (m, 1H), 4.38-4.36 (m, 1H), 3.92-3.88 (m, 1H), 3.77-3.74 (m, 1H), 3.06-3.02 (m, 1H), 2.95-2.93 (m, 1H), 2.81-2.79 (m, 1H), 2.67-2.63 (m, 1H), 2.41-2.36 (m, 1H), 2.13-2.00 (m, 4H), 1.60-1.58 (m, 2H).

MS m/z (ESI): 582.2 [M+1].

Embodiment 7: Preparation of Compound 7

30 mg of compound 4 was dissolved in 5 mL of methanol, added with 6 mg of Pd/C, and hydrogenated overnight at room temperature, filtered and concentrated to obtain compound 7 (29 mg).

MS m/z (ESI): 548.2 [M+1].

Embodiment 8: Preparation of Compound 8

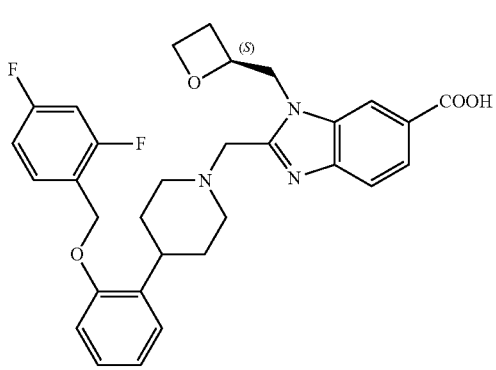

According to the similar synthetic method of embodiment 1, except adopting 1-(bromomethyl)-2-fluoro-4-fluorobenzene in step 3 of embodiment 1 instead of compound 1-5 (4-(bromomethyl)-3-fluorobenzonitrile), compound 8 was prepared in the same method as in embodiment 1.

$^1$H NMR (400 MHz, DMSO-$d_6$): 12.77 (brs, 1H), 8.28 (s, 1H), 7.82 (d, J=8.0 Hz, 1H), 7.66-7.60 (m, 2H), 7.37-7.32 (m, 1H), 7.20-7.09 (m, 4H), 6.95-6.92 (m, 1H), 5.13 (s, 2H), 5.05-4.99 (m, 1H), 4.82-4.77 (m, 1H), 4.67-4.64 (m, 1H), 4.50-4.49 (m, 1H), 4.38-4.36 (m, 1H), 3.96-3.92 (m, 1H), 3.81-3.77 (m, 1H), 3.00-2.97 (m, 1H), 2.87-2.84 (m, 2H), 2.71-2.69 (m, 1H), 2.44-2.40 (m, 1H), 2.22-2.10 (m, 2H), 1.67-1.58 (m, 4H).
MS m/z (ESI): 548.2 [M+1].

Embodiment 9: Preparation of Compound 9

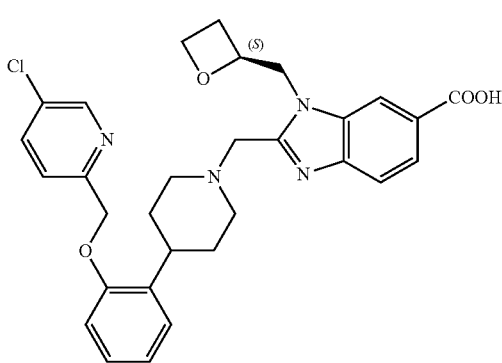

According to the similar synthetic method of embodiment 1, except adopting 2-(bromomethyl)-5-chloropyridine in step 3 of embodiment 1 instead of compound 1-5 (4-(bromomethyl)-3-fluorobenzonitrile), compound 9 was prepared in the same method as in embodiment 1.

$^1$H NMR (400 MHz, DMSO-$d_6$): 12.83 (brs, 1H), 8.66 (s, 1H), 8.35-8.39 (m, 2H), 8.10-8.05 (m, 1H), 7.90-7.83 (m, 1H), 7.66-7.56 (m, 2H), 7.21-7.14 (m, 2H), 7.01 (d, J=8.0 Hz, 1H), 5.21 (s, 2H), 5.12-5.05 (m, 1H), 4.82-4.75 (m, 1H), 4.67-4.60 (m, 1H), 4.53-4.49 (m, 1H), 4.38-4.36 (m, 1H), 4.00-3.87 (m, 1H), 3.76-3.74 (m, 1H), 3.01-2.86 (m, 3H), 2.71-2.65 (m, 1H), 2.44-2.22 (m, 2H), 1.95-1.89 (m, 1H), 1.77-1.63 (m, 4H). MS m/z (ESI): 547.2 [M+1].

Embodiment 10: Preparation of Compound 10

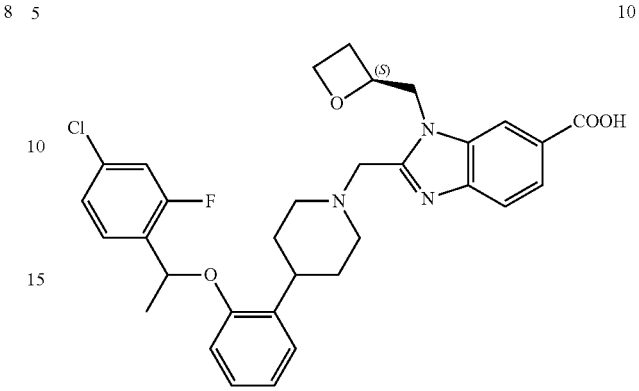

According to the similar synthetic method of embodiment 1, except adopting 4-chloro-1-(1-chloroethyl)-2-fluorobenzene in step 3 of embodiment 1 instead of compound 1-5 (4-(bromomethyl)-3-fluorobenzonitrile), compound 10 was prepared in the same method as in embodiment 1.

$^1$H NMR (400 MHz, DMSO-$d_6$): 12.71 (brs, 1H), 8.30 (s, 1H), 7.84 (d, J=8.0 Hz, 1H), 7.69 (d, J=8.0 Hz, 1H), 7.48-7.44 (m, 2H), 7.31 (d, J=8.0 Hz, 1H), 7.19 (d, J=8.0 Hz, 1H), 7.06 (t, J=8.0 Hz, 1H), 6.87 (t, J=8.0 Hz, 1H), 6.78 (d, J=8.0 Hz, 1H), 5.65 (q, J=8.0 Hz, 1H), 5.12-5.10 (m, 1H), 4.74-4.70 (m, 1H), 4.51-4.48 (m, 1H), 4.40-4.37 (m, 1H), 4.04-3.99 (m, 1H), 3.87-3.75 (m, 1H), 2.98-2.90 (m, 3H), 2.72-2.70 (m, 1H), 2.43-2.41 (m, 1H), 2.35-2.30 (m, 2H), 1.68-1.65 (m, 4H), 1.61 (d, J=8.0 Hz, 3H).
MS m/z (ESI): 578.2 [M+1].

Embodiment 11: Preparation of Compound 11

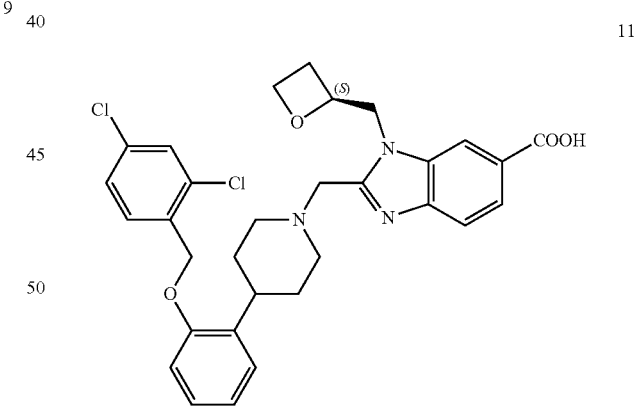

According to the similar synthesis method of embodiment 1, compound 11 was prepared.

$^1$H NMR (400 MHz, DMSO-$d_6$): 12.72 (brs, 1H), 8.28 (s, 1H), 7.78 (d, J=8.0 Hz, 1H), 7.72 (s, 1H), 7.64 (d, J=8.0 Hz, 1H), 7.60 (d, J=8.0 Hz, 1H), 7.53 (d, J=8.0 Hz, 1H), 7.22-7.18 (m, 2H), 7.06 (d, J=8.0 Hz, 1H), 6.96-6.93 (m, 1H), 5.15 (s, 2H), 5.10-5.05 (m, 1H), 4.81-4.77 (m, 1H), 4.67-4.63 (m, 1H), 4.50-4.48 (m, 1H), 4.37-4.33 (m, 1H), 4.02-3.93 (m, 2H), 3.82-3.80 (m, 1H), 3.00-2.88 (m, 3H), 2.69-2.65 (m, 1H), 2.43-2.39 (m, 1H), 2.22-2.16 (m, 2H), 1.70-1.61 (m, 4H).
MS m/z (ESI): 580.2 [M+1].

Embodiment 12: Preparation of Compound 12

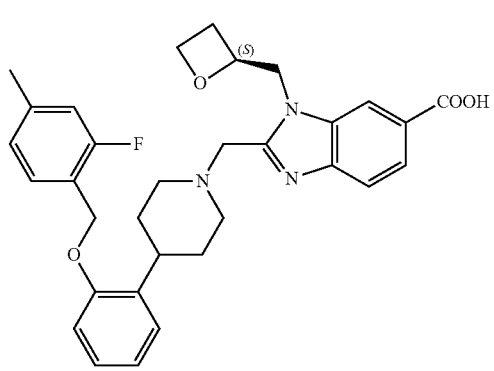

According to the similar synthesis method of embodiment 1, compound 12 was prepared.

$^1$H NMR (400 MHz, DMSO-d$_6$): 12.77 (brs, 1H), 8.29 (s, 1H), 7.83 (d, J=8.0 Hz, 1H), 7.68 (d, J=8.0 Hz, 1H), 7.43-7.40 (m, 1H), 7.19-7.17 (m, 2H), 7.11-7.05 (m, 3H), 6.92-6.90 (m, 1H), 5.10 (s, 2H), 4.81-4.79 (m, 1H), 4.67-4.63 (m, 1H), 4.37-4.36 (m, 1H), 4.04-3.84 (m, 3H), 3.02-2.97 (m, 1H), 2.89-2.84 (m, 2H), 2.73-2.65 (m, 1H), 2.43-2.40 (m, 1H), 2.33 (s, 3H), 2.22-2.16 (m, 2H), 1.69-1.60 (m, 4H).

MS m/z (ESI): 544.2 [M+1].

Embodiment 13: Preparation of Compound 13

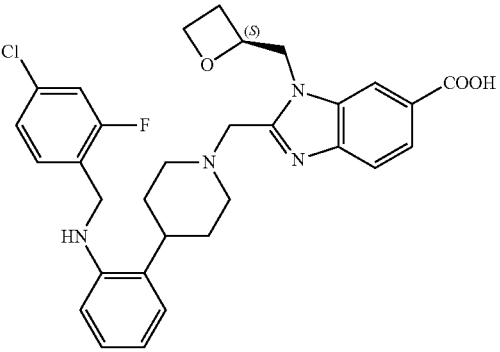

According to the similar synthesis method of embodiment 1, compound 13 was prepared.

$^1$H NMR (400 MHz, DMSO-d$_6$): 12.72 (brs, 1H), 8.28 (s, 1H), 7.81 (d, J=8.0 Hz, 1H), 7.67 (d, J=8.0 Hz, 1H), 7.61-7.53 (m, 2H), 7.39 (d, J=8.0 Hz, 1H), 7.22-7.18 (m, 1H), 7.05-7.02 (m, 1H), 6.77-6.73 (m, 1H), 5.17 (s, 2H), 5.08-5.05 (m, 1H), 4.78-4.76 (m, 1H), 4.66-4.63 (m, 1H), 4.51-4.46 (m, 1H), 4.39-4.35 (m, 1H), 3.96-3.93 (m, 1H), 3.81-3.78 (m, 1H), 2.99-2.97 (m, 1H), 2.84-2.68 (m, 3H), 2.40-2.38 (m, 1H), 2.19-2.14 (m, 2H), 1.66-1.63 (m, 4H);

MS m/z (ESI): 582.2 [M+1].

Embodiment 14: Preparation of Compound 14

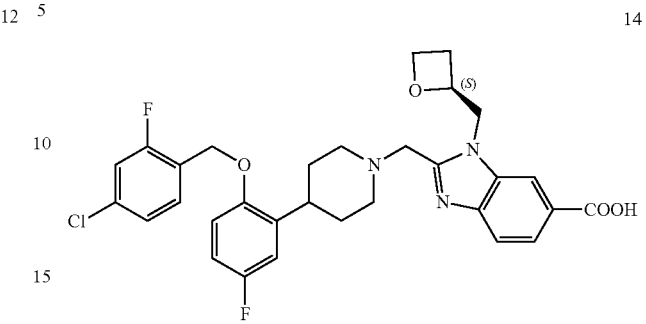

According to the similar synthesis method of embodiment 1, compound 14 was prepared.

$^1$H NMR (400 MHz, DMSO-d$_6$): 12.67 (brs, 1H), 8.28 (s, 1H), 7.82 (d, J=8.0 Hz, 1H), 7.66 (d, J=8.0 Hz, 1H), 7.59-7.51 (m, 2H), 7.38 (d, J=8.0 Hz, 1H), 7.13-7.09 (m, 1H), 7.04-7.00 (m, 2H), 5.13 (s, 2H), 5.09-5.07 (m, 1H), 4.83-4.76 (m, 1H), 4.67-4.63 (m, 1H), 4.50-4.48 (m, 1H), 4.38-4.36 (m, 1H), 4.04-4.02 (m, 1H), 4.00-3.95 (m, 1H), 3.92-3.85 (m, 1H), 3.00-2.96 (m, 1H), 2.85-2.80 (m, 2H), 2.72-2.70 (m, 1H), 2.45-2.41 (m, 1H), 2.22-2.21 (m, 2H), 1.66-1.62 (m, 4H).

MS m/z (ESI): 582.2 [M+1].

Embodiment 15: Preparation of Compound 15

According to the similar synthesis method of embodiment 1, compound 15 was prepared.

$^1$H NMR (400 MHz, DMSO-d$_6$): 12.72 (brs, 1H), 8.29 (s, 1H), 7.83 (d, J=8.0 Hz, 1H), 7.67 (s, 1H), 7.41 (d, J=12.0 Hz, 1H), 7.30-7.22 (m, 2H), 7.05 (d, J=8.0 Hz, 1H), 6.93-6.90 (m, 1H), 6.58-6.56 (m, 1H), 6.32 (d, J=8.0 Hz, 1H), 5.84 (brs, 1H), 5.11-5.10 (m, 1H), 4.86-4.80 (m, 1H), 4.70-4.67 (m, 1H), 4.51-4.50 (m, 1H), 4.36-4.33 (m, 3H), 4.04-3.99 (m, 2H), 3.86-3.83 (m, 1H), 3.05-3.02 (m, 1H), 2.92-2.85 (m, 1H), 2.75-2.70 (m, 2H), 2.42-2.34 (m, 3H), 1.83-1.77 (m, 2H), 1.60-1.55 (m, 2H).

MS m/z (ESI): 563.2 [M+1].

Embodiment 16: Preparation of Compound 16

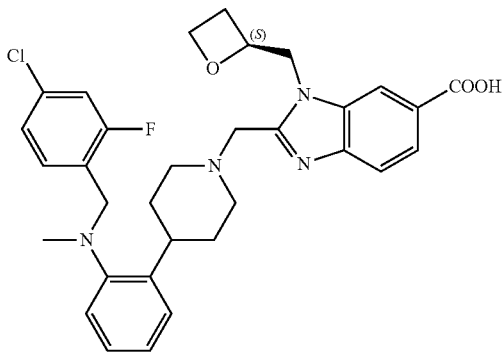

According to the similar synthesis method of embodiment 1, compound 16 was prepared.
MS m/z (ESI): 577.2 [M+1].

Embodiment 17: Preparation of Compound 17

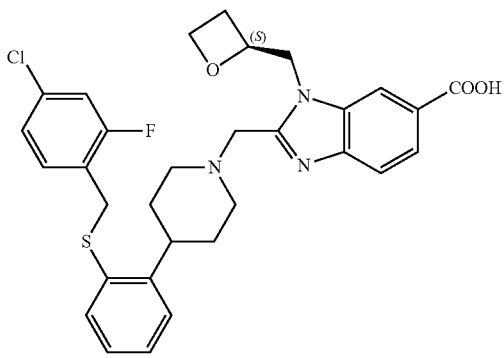

According to the similar synthesis method of embodiment 1, compound 17 was prepared.
MS m/z (ESI): 580.2 [M+1].

Embodiment 18: Preparation of Compound 18

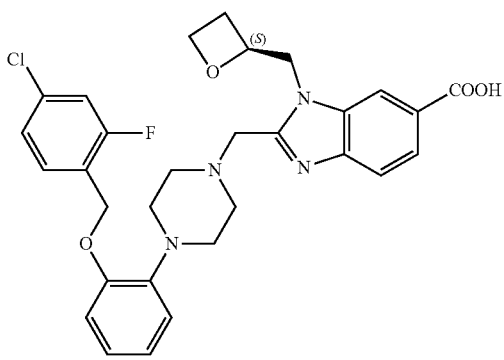

According to the similar synthesis method of embodiment 1, compound 18 was prepared.
$^1$H NMR (400 MHz, DMSO-$d_6$): 8.24 (s, 1H), 7.83 (d, J=8.0 Hz, 1H), 7.68 (d, J=8.0 Hz, 1H), 7.57-7.54 (m, 1H), 7.42-7.39 (m, 1H), 7.30-7.28 (m, 1H), 7.02-6.99 (m, 1H), 6.95-6.90 (m, 3H), 5.07 (s, 2H), 4.77-4.70 (m, 2H), 4.61-4.57 (m, 2H), 4.48-4.44 (m, 2H), 4.33-4.30 (m, 2H), 2.98-2.94 (m, 3H), 2.67-2.65 (m, 1H), 2.62-2.56 (m, 3H), 2.40-2.35 (m, 2H).
MS m/z (ESI): 565.2 [M+1].

Embodiment 19: Preparation of Compound 19

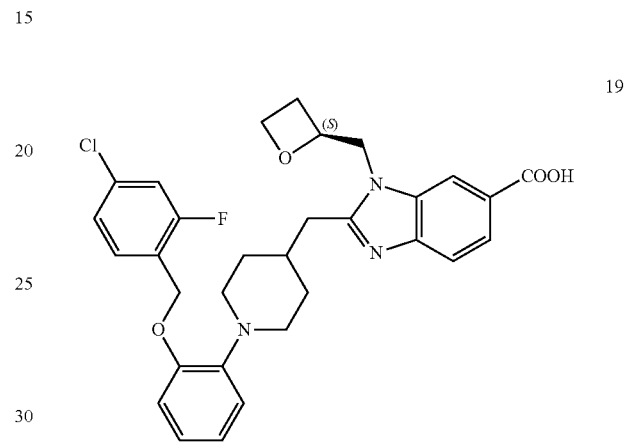

According to the similar synthesis method of embodiment 1, compound 19 was prepared.
MS m/z (ESI): 564.2 [M+1].

Embodiment 20: Preparation of Compound 20

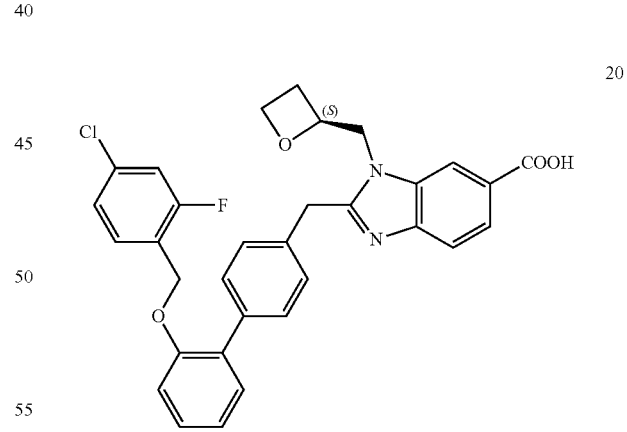

According to the similar synthesis method of embodiment 1, compound 20 was prepared.
$^1$H NMR (400 MHz, DMSO-$d_6$): 12.74 (brs, 1H), 8.24 (s, 1H), 7.80 (d, J=8.0 Hz, 1H), 7.64 (d, J=8.0 Hz, 1H), 7.47-7.44 (m, 4H), 7.33-7.31 (m, 4H), 7.23-7.20 (m, 2H), 7.06-7.00 (m, 1H), 5.14 (s, 2H), 4.91-4.88 (m, 1H), 4.68-4.62 (m, 1H), 4.54-4.50 (m, 1H), 4.45-4.40 (m, 3H), 4.34-4.31 (m, 1H), 2.59-2.55 (m, 1H), 2.30-2.34 (m, 1H).
MS m/z (ESI): 557.1 [M+1].

Embodiment 21: Preparation of Compound 21

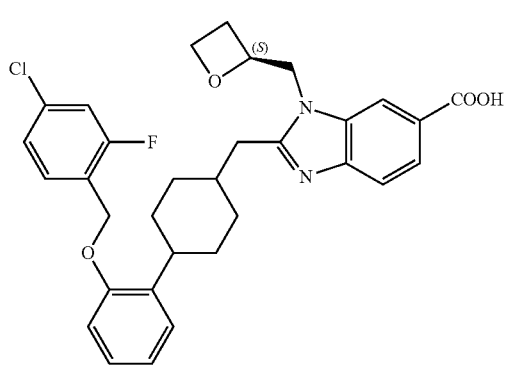

According to the similar synthesis method of embodiment 1, compound 21 was prepared.
MS m/z (ESI): 563.2 [M+1].

Embodiment 22: Preparation of Compound 22

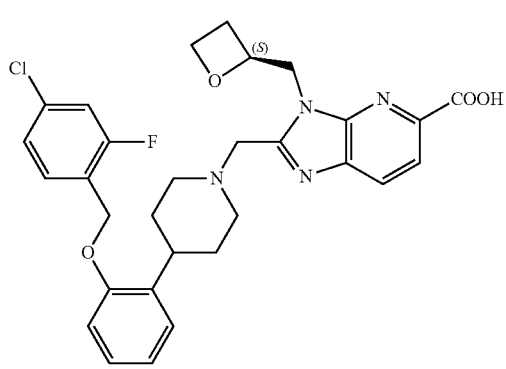

According to the similar synthesis method of embodiment 1, compound 22 was prepared.
MS m/z (ESI): 565.2 [M+1].

Embodiment 23: Preparation of Compound 23

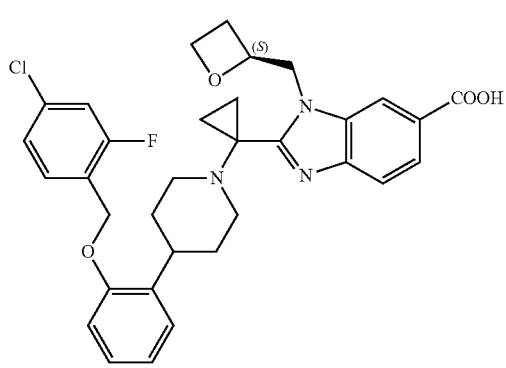

According to the similar synthesis method of embodiment 1, compound 23 was prepared.
MS m/z (ESI): 590.2 [M+1].

Embodiment 24: Preparation of Compound 24

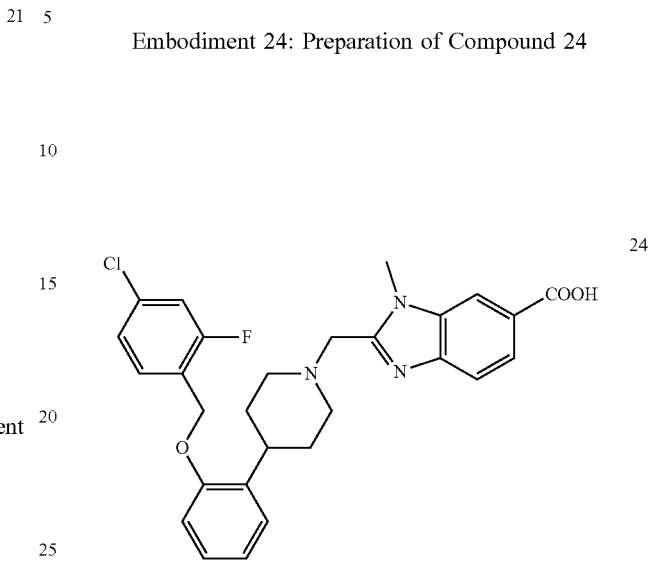

According to the similar synthesis method of embodiment 1, compound 24 was prepared.
MS m/z (ESI): 508.1 [M+1].

Embodiment 25: Preparation of Compound 25

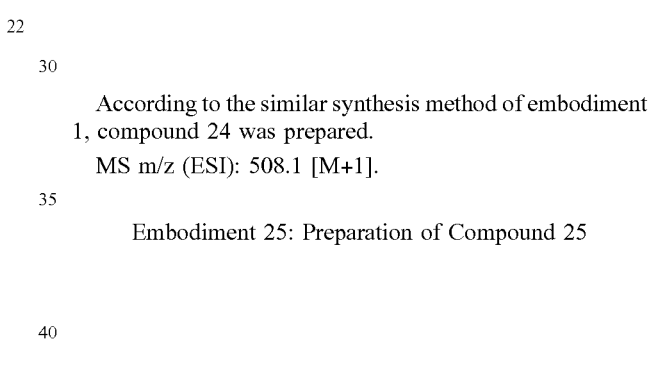

According to the similar synthesis method of embodiment 1, compound 25 was prepared.
MS m/z (ESI): 602.2 [M+1].

Embodiment 26: Preparation of Compound 26

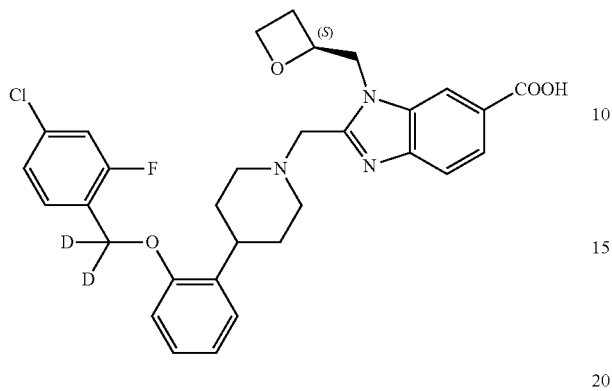

According to the similar synthesis method of embodiment 1, compound 26 was prepared.
MS m/z (ESI): 566.2 [M+1].

Embodiment 27: Preparation of Compound 27

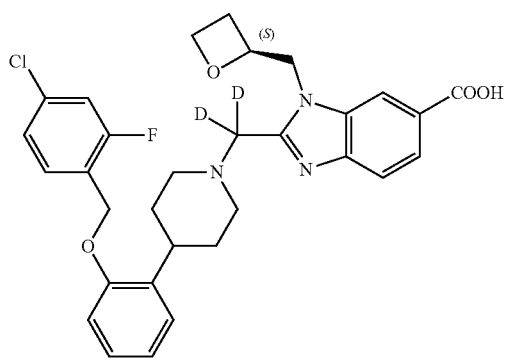

According to the similar synthesis method of embodiment 1, compound 26 was prepared.
MS m/z (ESI): 566.2 [M+1].

Embodiment 28: Preparation of Compound 28

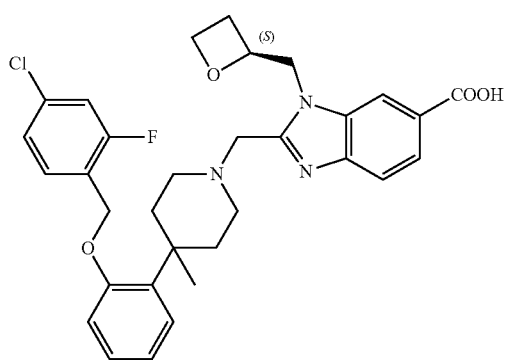

According to the similar synthesis method of embodiment 1, compound 28 was prepared.
MS m/z (ESI): 578.2 [M+1].

Embodiment 29: Preparation of Compound 29

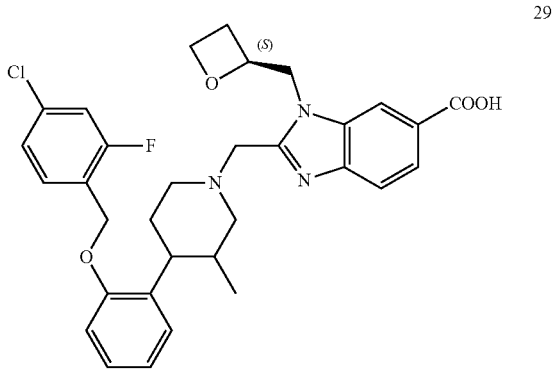

According to the similar synthesis method of embodiment 1, compound 29 was prepared.
MS m/z (ESI): 578.2 [M+1].

Embodiment 30: Preparation of Compound 30

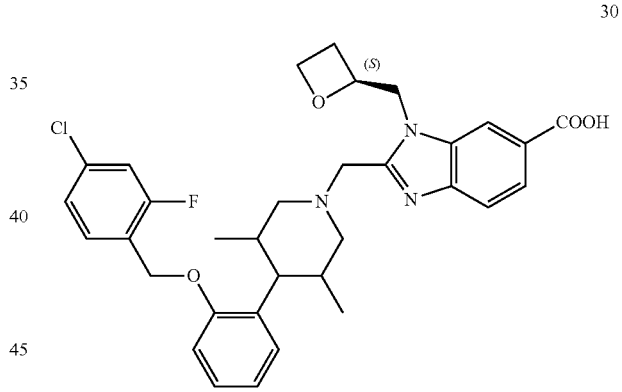

According to the similar synthesis method of embodiment 1, compound 30 was prepared.
MS m/z (ESI): 592.2 [M+1].

Test Embodiment 1: Activity Test of GLP-1R cAMP Assay

This experiment aims to verify the agonistic activity of the compound of the present disclosure on human GLP-1R receptor.

Main Reagents:

cAMP Detection Kit, Cisbio (Cat # 62AM4PEJ)
1M HEPES, Invitrogen (Cat # 15630-106)
1X HBSS, Invitrogen (Cat # 14025)
BSA, Sigma (Cat # B2064-100G)
IBMX, Sigma (Cat # I5879)
7-37, Hao Yuan (Cat # HY-P0055)

Culture Medium:

| Target | Host cell line | Clone |
|---|---|---|
| GLP-1R | HEK293 | N/A |

Main Consumables and Instruments:

OptiPlate-384, White, PerkinElmer (Cat # 6007290);
384 well plate for Echo, Labcyte (Cat # P-05525);
En Vision, PerkinElmer;
Vi-cell counter, Beckman(Cat # Vi-CELL ™ XR Cell Viability Analyzer)

Experimental Method:
a) Preparation of Compound Source Plate:
Compounds were diluted 4-fold starting at 100 μM from DMSO using Bravo for a total of 10 points.
The reference compound polypeptide GLP-1 (7-37) was diluted 4-fold starting from 500 nM in DMSO using Bravo for a total of 10 points.
b) Preparation of Cell Suspension:
1) 1 vial of GLP-1R cells was quickly thawed in a 37° C. water bath.
2) The suspension of the cells was transferred to 10 mL of HBSS in a 15 mL conical tube.
3) The cells were centrifuged at 1000 rpm for 5 min at room temperature to precipitate the cells.
4) The supernatant was gently aspirated, and being careful not to aspirate the cells.
5) The cells were relaxed by flicking the precipitation, and then the cell precipitation was re-suspended in 10 mL of HBSS. A sterile pipette was used to move fluid up and down to remove clumps.
6) The concentration of cells was counted and the cell viability on Vi-cell was determined.
7) GLP-1R cells were re-suspended in the test buffer at a concentration of 2.0×E5/mL cells.
8) 10 μL of GLP-1R cell was transferred to OptiPlate-384 well plate.
c) Transfer of Compound:
1) 100 nL of compound was transferred to OptiPlate-384 plate using Echo Transfer.
2) The plate was rotated at 1000 rpm for 5 seconds.
d) HTRF cAMP Analysis of Agonists:
1) The plate was incubated at room temperature for 30 minutes before adding detection reagents.
2) An electric multi-channel pipette was used to add 10 μL of detection reagents respectively.
3) The 384 well plate was covered with TopSeal-A membrane and incubated for 60 min at room temperature.
TopSeal-A was unloaded and read on EnVision.
The specific test data are shown in Table 1 below.

TABLE 1

| Compound | $EC_{50}$, (nM) |
|---|---|
| 1 | 3.4 |
| 2 | 0.8 |
| 3 | 0.9 |
| 4 | 0.7 |
| 5 | 15 |
| 6 | 8.1 |
| 7 | 5 |
| 8 | 3.2 |
| 9 | 34.8 |

TABLE 1-continued

| Compound | $EC_{50}$, (nM) |
|---|---|
| 10 | 26 |
| 11 | 2.9 |
| 12 | 1.0 |
| 13 | 5.8 |
| 14 | 3.7 |
| 15 | 7.5 |
| 16 | >100 |
| 17 | 53 |
| 18 | 10.7 |
| 19 | >100 |
| 20 | 24.6 |
| 21 | >100 |
| 22 | 2.1 |
| 23 | >100 |
| 24 | >100 |
| 25 | >100 |
| 26 | 1.8 |
| 27 | 2.3 |
| 28 | >100 |
| 29 | >100 |
| 30 | >100 |
| PF-06882961 | 0.8 |
| Ref-01 | 1 |
| Ref-02 | 1 |

Conclusion: The compounds of the present disclosure show good GLP-1R receptor agonistic activity.

Test Embodiment 2: Pharmacokinetic Evaluation in Rats

The drug concentrations in the plasma of rats were tested at different times after the administration of the compounds by gavage using rats as test animals. The pharmacokinetic behavior of the compounds of the present disclosure in rats was studied and their pharmacokinetic characteristics were evaluated. In each group of embodiments, 3 rats with similar body weight were selected and administered orally at a dose of 10 mg/kg for a single administration. Blood was collected from animals at 15 min, 30 min, 1 h, 2 h, 4 h, 6 h, 8 h, 12 h, 24 h time points after administration. The LC-MS/MS analysis method was used to detect the content of the compound in plasma, and the lower limit of quantification of the method was 20 ng/mL. Concentration data in plasma was counted using the metabolic kinetic data analysis software WinNonlin 7.0, and the pharmacokinetic parameters were calculated using the non-compartmental analysis (NCA), as shown in Table 2 below.

Experimental Protocol:
Experimental drugs: Compounds of the present disclosure and reference compounds.

Drug configuration: A certain amount of drug was taken, added with 2% Klucel LF+0.1% Tween 80 aqueous solution to prepare a clear solution or a uniform suspension.

Administration: Rats were administered by gavage after overnight fasting at a dose of 10 mg/kg.

Operation: Rats were administered by gavage, and blood was collected from the tail vein before administration and 15 min, 30 min, 1 h, 2 h, 4 h, 6 h, 8 h, 12 h, 24 h after administration, placed in heparinized sample tubes, centrifuged at 4° C., 3500 rpm for 10 min to separate plasma, stored at −20° C., and fed 2 hours after administration.

Determination of the content of test compounds in rat plasma after drug administration by gavage: 50 μL of plasma samples were thawed at room temperature, added with 130 μL of internal standard working solution (1000 ng/mL, acetonitrile, tolbutamide), vortexed for about 1 min and then centrifuged for 10 min at 4° C. and 13000 rpm. 50 μL of supernatant was mixed with 100 μL of 50% acetonitrile in water, and then the sample was injected for LC/MS/MS analysis.

The results of pharmacokinetic parameters are shown in Table 2.

TABLE 2

Drug metabolism data of rats

| Compound | Dose (mg/kg) | $T_{max}$ (h) | $C_{max}$ (ng/mL) | $AUC_{0-\infty}$ (ng · h/mL) | $T_{1/2}$ (h) |
|---|---|---|---|---|---|
| 3 | 10 | 0.25 | 1160 | 1033 | 2.58 |
| 4 | 10 | 0.83 | 90 | 417 | 2.11 |
| 12 | 10 | 0.25 | 1018 | 1319 | 2.68 |
| PF-06882961 | 10 | 0.42 | 55 | 179 | 6.88 |
| Ref-01 | 10 | 0.33 | 105 | 351 | 3.20 |
| Ref-02 | 10 | 0.25 | 171 | 229 | 5.52 | to detect the content of the compound in plasma, and the lower limit of quantification of the method was 20 ng/mL. Concentration data in plasma was counted using the metabolic kinetic data analysis software WinNonlin 7.0, and the pharmacokinetic parameters were calculated using the non-compartmental analysis (NCA), as shown in Table 3 below.

Determination of the content of test compounds in the plasma of cynomolgus monkeys after drug administration: After blood samples were collected, placed in a marked ice-bath centrifuge tube, and rapidly centrifuged to separate the plasma. Centrifugation conditions: 4000 rpm, 10 minutes, 4° C., and plasma was stored at −40° C. or less for testing.

The results of pharmacokinetic parameters are shown in Table 3.

| Compound | Dose (mg/kg) | $T_{max}$ (h) | $C_{max}$ (ng/mL) | $C_{24\,h}$ (ng/mL) | $AUC_{0-24\,h}$ (ng · h/mL) | $T_{1/2}$ (h) | Cl (mL/h/kg) | F (%) |
|---|---|---|---|---|---|---|---|---|
| 3 | 1, IV | 0.083 | 1590 | — | 898 | 0.98 | 1154 | |
|  | 50, PO | 2.5 | 2435 | 597 | 23010 | 22.6 | | 51.2 |
| PF-06882961 | 1, IV | 0.083 | 2225 | — | 1074 | 1.14 | 956 | |
|  | 50, PO | 1.75 | 2046 | 41.4 | 4329 | 10.9 | | 8.0 |

Conclusion: Compared with the reference compounds PF-06882961, Ref-01 and Ref-02, the compounds of the present disclosure have better absorption, higher drug exposure in blood, and have excellent drug metabolism properties.

Test Embodiment 3: Pharmacokinetic Evaluation of Cynomolgus Monkey

The drug concentrations in the plasma of cynomolgus monkeys were tested at different times after intravenous injection and oral administration of the compounds using cynomolgus monkeys as test animals. The pharmacokinetic behavior of the compounds of the present disclosure in cynomolgus monkeys was studied and their pharmacokinetic characteristics were evaluated. In each group of embodiments, 2 cynomolgus monkeys with similar body weight were selected, administered at a dose of 1 mg/kg by intravenous injection and at a dose of 50 mg/kg by oral administration for a single administration.

Age of cynomolgus monkeys at the time of administration: about 2-4 years old; body weight: 3.0-4.6 kg at the beginning of administration; 4 monkeys; sex: male.

Intravenous group: The final concentration of 0.5 mg/mL was prepared for intravenous administration, and the preparation solvent was 5% DMSO+45% PEG400+50% water, and the preparation was in a clarified solution.

Oral group: The final concentration of 10 mg/mL was prepared for oral administration, and the preparation solvent was 5% DMSO+45% PEG400+50% water, and the preparation was in homogeneous suspension.

Blood was collected from animals at 5 min, 15 min, 30 min, 1 h, 2 h, 4 h, 7 h, 12 h, 24 h time points after administration. The LC-MS/MS analysis method was used Conclusion: Compared with the reference compound PF-06882961, under the same preparation and dose, the compound of the present disclosure has significantly better pharmacokinetic properties in cynomolgus monkeys. After oral administration of the compound of the present disclosure, the compound has higher blood exposure and still has high blood concentrations after 24 hours, has significantly better oral bioavailability and is suitable for oral administration.

The above embodiments are only to illustrate the technical concept and characteristics of the present disclosure, and the purpose is to enable those skilled in the art to understand the content of the present disclosure and implement it accordingly, and not to limit the protection scope of the present disclosure. All equivalent changes or modifications made according to the spirit of the present disclosure shall fall within the protection scope of the present disclosure.

What is claimed is:

1. A compound represented by the following formula (I) or a pharmaceutically acceptable salt thereof,

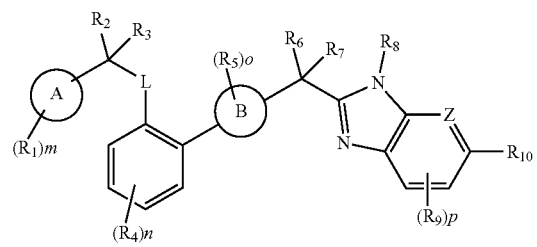

wherein,
A is phenyl or 5- to 6-membered heteroaryl containing one or two heteroatoms selected from O and N;
$R_1$ is —H, halogen, —CN, —OH, deuterium, —$C_{1-6}$ alkyl, —$C_{1-6}$ alkoxy, —$C_{2-6}$ alkenyl, —$C_{2-6}$ alkynyl, —$C_{6-10}$ aryl or —$C_{5-10}$ heteroaryl containing one or two heteroatoms selected from O and N; the —$C_{1-6}$ alkyl, —$C_{1-6}$ alkoxy, —$C_{2-6}$ alkenyl or —$C_{2-6}$ alkynyl is substituted by 0-3 F;

subscript m is an integer of 0, 1, 2 or 3;

$R_2$, $R_3$ are each independently —H, deuterium, or $C_{1-6}$ alkyl; or $R_2$, $R_3$ together with the carbon atom to which they are attached form a 3- to 6-membered cycloalkyl or heterocycloalkyl containing one or two heteroatoms selected from O and N;

L is —O—, —S—, —$NR_{11}$— or —$C(R_{11}R_{12})$—; the $R_{11}$, $R_{12}$ are hydrogen or —$C_{1-6}$ alkyl;

$R_4$ is halogen, —CN, —OH, deuterium, —$C_{1-6}$ alkyl, —$C_{1-6}$ alkoxy, —$C_{2-6}$ alkenyl or —$C_{2-6}$ alkynyl;
the —$C_{1-6}$ alkyl, —$C_{1-6}$ alkoxy, —$C_{2-6}$ alkenyl or —$C_{2-6}$ alkynyl is substituted by 0-3 F;

subscript n is an integer of 0, 1 or 2;

B is

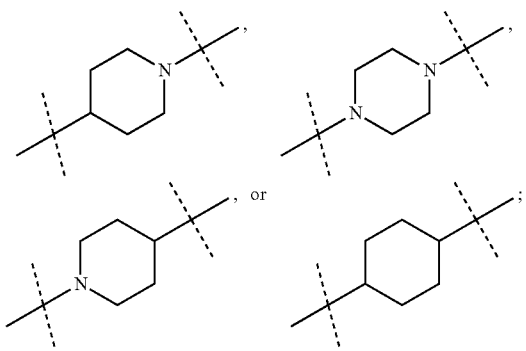

$R_5$ is —H, halogen, —CN, —OH, deuterium, —$C_{1-6}$ alkyl, —$C_{1-6}$ alkoxy, —$C_{2-6}$ alkenyl or —$C_{2-6}$ alkynyl; the —$C_{1-6}$ alkyl, —$C_{1-6}$ alkoxy, —$C_{2-6}$ alkenyl or —$C_{2-6}$ alkynyl is substituted by 0-3 F;

subscript o is an integer of 0, 1 or 2;

$R_6$, $R_7$ are each independently —H, deuterium, or —$C_{1-6}$ alkyl; or $R_6$, $R_7$ together with the carbon atom to which they are attached form a 3- to 6-membered cycloalkyl or a 3- to 6-membered heterocycloalkyl containing one or two heteroatoms selected from O and N; or $R_6$, B ring together with the carbon atom to which they are attached form a 3- to 6-membered cycloalkyl or a 3- to 6-membered heterocycloalkyl containing one or two heteroatoms selected from O and N;

$R_8$ is —$C_{1-3}$ alkyl, -methylene-$C_{3-6}$ cycloalkyl or -methylene-$C_{4-6}$ heterocycloalkyl containing one or two heteroatoms selected from O and N; wherein, the —$C_{1-3}$ alkyl, -methylene-$C_{3-6}$ cycloalkyl or -methylene-$C_{4-6}$ heterocycloalkyl containing one or two heteroatoms selected from O and N is unsubstituted or substituted by one or more substituents selected from halogen, —CN, —OH, deuterium, —$C_{1-6}$ alkyl, —$C_{1-6}$ alkoxy, —$C_{2-6}$ alkenyl, —$C_{2-6}$ alkynyl and 5- to 6-membered heteroaryl containing one or two heteroatoms selected from O and N;

Z is N or $CR_{13}$;

$R_9$ is hydrogen, halogen, —CN, —OH, deuterium, —$C_{1-6}$ alkyl, —$C_{1-6}$ alkoxy, —$C_{2-6}$ alkenyl or —$C_{2-6}$ alkynyl; the —$C_{1-6}$ alkyl, —$C_{1-6}$ alkoxy, —$C_{2-6}$ alkenyl or —$C_{2-6}$ alkynyl is substituted by 0-3 F;

subscript p is an integer of 0, 1 or 2;

$R_{10}$ is —COOH or an isostere of carboxyl;

$R_{13}$ is hydrogen, halogen, —CN, —OH, deuterium, —$C_{1-6}$ alkyl, —$C_{1-6}$ alkoxy, —$C_{2-6}$ alkenyl or —$C_{2-6}$ alkynyl; the —$C_{1-6}$ alkyl, —$C_{1-6}$ alkoxy, —$C_{2-6}$ alkenyl or —$C_{2-6}$ alkynyl is substituted by 0-3 F;

the halogen is selected from F, Cl and Br.

2. The compound or the pharmaceutically acceptable salt thereof according to claim 1, wherein, the compound or the pharmaceutically acceptable salt thereof has a structure represented by the following formula (II):

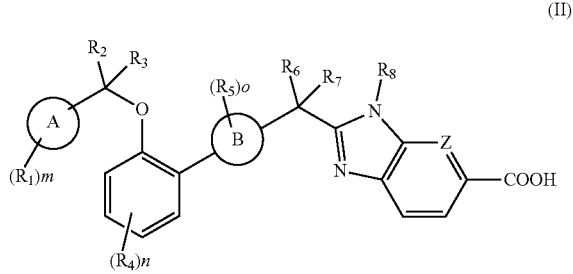

wherein,

A is phenyl or pyridyl;

$R_1$ is halogen, —CN, —OH, deuterium, —$C_{1-6}$ alkyl, —$C_{1-6}$ alkoxy, —$C_{2-6}$ alkenyl, or —$C_{2-6}$ alkynyl; the —$C_{1-6}$ alkyl, —$C_{1-6}$ alkoxy, —$C_{2-6}$ alkenyl or —$C_{2-6}$ alkynyl is substituted by 0-3 F;

subscript m is an integer of 0, 1 or 2;

$R_2$, $R_3$ are each independently —H, deuterium, or $C_{1-6}$ alkyl;

$R_4$ is halogen, —CN, —OH, deuterium, —$C_{1-6}$ alkyl or —$C_{1-6}$ alkoxy;

subscript n is an integer of 0 or 1;

B is

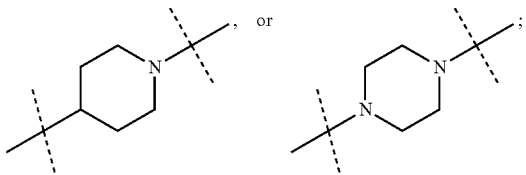

$R_5$ is halogen, —OH, —$C_{1-6}$ alkyl or —$C_{1-6}$ alkoxy;

subscript o is an integer of 0, 1 or 2;

$R_6$, $R_7$ are each independently —H, deuterium, or $C_{1-6}$ alkyl; or $R_6$, $R_7$ together with the carbon atom to which they are attached form a 3- to 6-membered cycloalkyl or a 3- to 6-membered heterocycloalkyl containing one or two heteroatoms selected from O and N;

$R_8$ is —$C_{1-3}$ alkyl, -methylene-$C_{3-6}$ cycloalkyl or -methylene-$C_{4-6}$ heterocycloalkyl containing one or two heteroatoms selected from O and N; wherein, the —$C_{1-3}$ alkyl, -methylene-$C_{3-6}$ cycloalkyl or -methylene-$C_{4-6}$ heterocycloalkyl containing one or two heteroatoms selected from O and N is unsubstituted or substituted by one or more substituents selected from halogen, —CN, —OH, deuterium, —$C_{1-6}$ alkyl, —$C_{1-6}$ alkoxy, —$C_{2-6}$ alkenyl, —$C_{2-6}$ alkynyl and 5- to 6-membered heteroaryl containing one or two heteroatoms selected from O and N;

Z is N or $CR_{13}$;

$R_{13}$ is hydrogen, halogen, —CN, —OH, deuterium, —$C_{1-6}$ alkyl or —$C_{1-6}$ alkoxy.

3. The compound or the pharmaceutically acceptable salt thereof according to claim 1, wherein, the compound or the pharmaceutically acceptable salt thereof has a structure represented by the following formula (III):

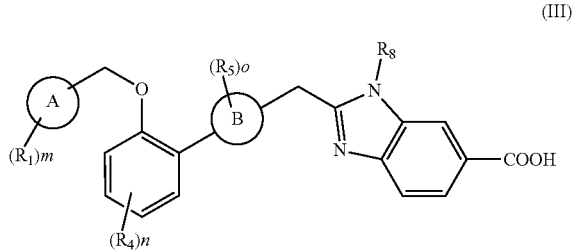

(III)

wherein,
$R_1$ is halogen, —CN, —OH, deuterium, —$C_{1-6}$ alkyl, —$C_{1-6}$ alkoxy, —$C_{2-6}$ alkenyl, or —$C_{2-6}$ alkynyl; the —$C_{1-6}$ alkyl, —$C_{1-6}$ alkoxy, —$C_{2-6}$ alkenyl or —$C_{2-6}$ alkynyl is substituted by 0-3 F;
subscript m is an integer of 1 or 2;
A is phenyl, or pyridyl;
$R_4$ is halogen, —OH, deuterium, —$C_{1-6}$ alkyl or —$C_{1-6}$ alkoxy;
subscript n is an integer of 0 or 1;
B is

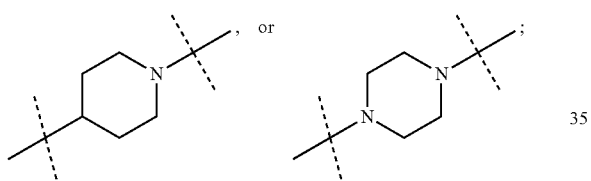

$R_5$ is halogen, —OH, —$C_{1-6}$ alkyl or —$C_{1-6}$ alkoxy;
subscript o is an integer of 0, 1 or 2;
$R_8$ is —$C_{1-3}$ alkyl, -methylene-$C_{3-6}$ cycloalkyl or -methylene-$C_{4-6}$ heterocycloalkyl.

4. The compound or the pharmaceutically acceptable salt thereof according to claim 1, wherein, the compound or the pharmaceutically acceptable salt thereof has a structure represented by the following formula (IV):

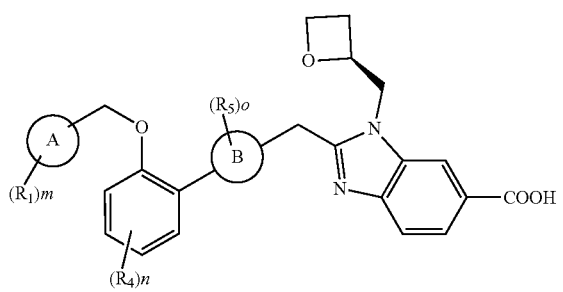

(IV)

wherein,
$R_1$ is halogen, —CN, —OH, deuterium, —$C_{1-6}$ alkyl, —$C_{1-6}$ alkoxy, —$C_{2-6}$ alkenyl, or —$C_{2-6}$ alkynyl; the —$C_{1-6}$ alkyl, —$C_{1-6}$ alkoxy, —$C_{2-6}$ alkenyl or —$C_{2-6}$ alkynyl is substituted by 0-3 F;

subscript m is an integer of 1 or 2;
A is phenyl, or pyridyl;
$R_4$ is halogen, —OH, deuterium, —$C_{1-6}$ alkyl or —$C_{1-6}$ alkoxy;
subscript n is an integer of 0 or 1;
B is

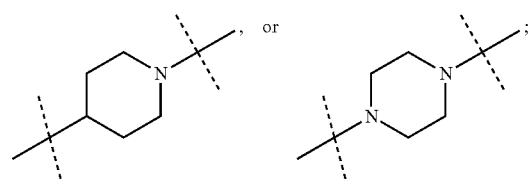

$R_5$ is —$C_{1-6}$ alkyl;
subscript o is an integer of 0 or 1.

5. The compound or the pharmaceutically acceptable salt thereof according to claim 4, wherein, in the structure of the compound represented by formula (IV) or the pharmaceutically acceptable salt thereof, $R_1$ is —F, —Cl, —Br, —CN, —$C_{1-6}$ alkyl, —$C_{1-6}$ alkoxy, —$C_{2-6}$ alkenyl or —$C_{2-6}$ alkynyl;
subscript m is 2;
A is phenyl;
$R_4$ is —F, or —Cl;
B is

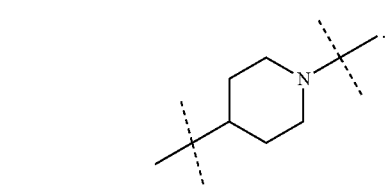

6. The compound or the pharmaceutically acceptable salt thereof according to claim 4, wherein, subscript o is 0.

7. The compound or the pharmaceutically acceptable salt thereof according to claim 1, wherein the compound is selected from one of the following compounds:

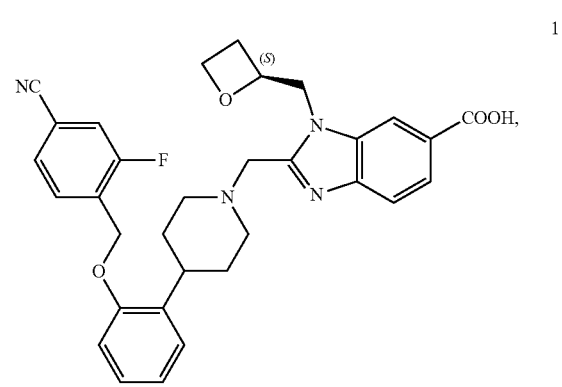

45
-continued

46
-continued

10
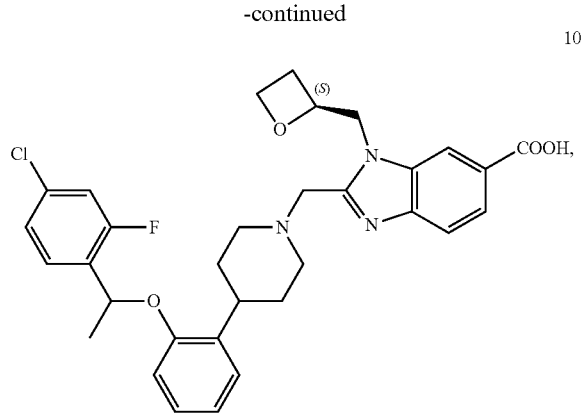
11
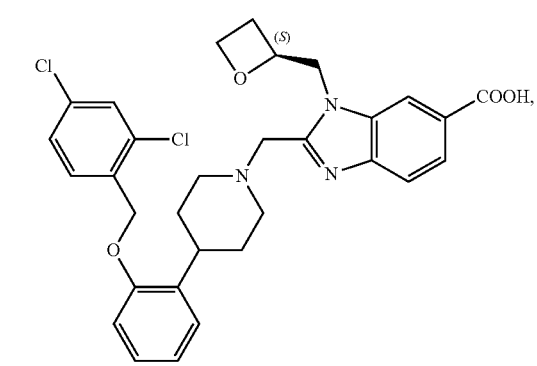
12
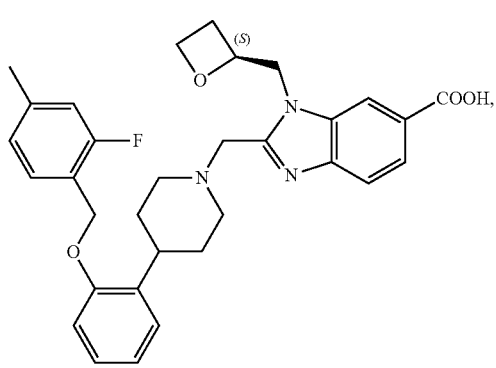
13
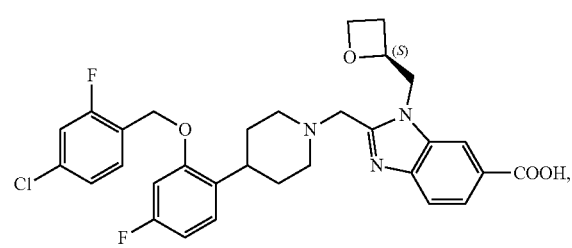
14
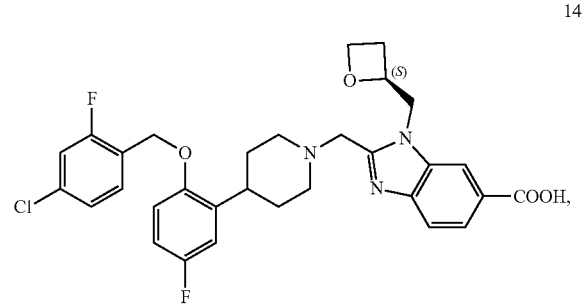
15
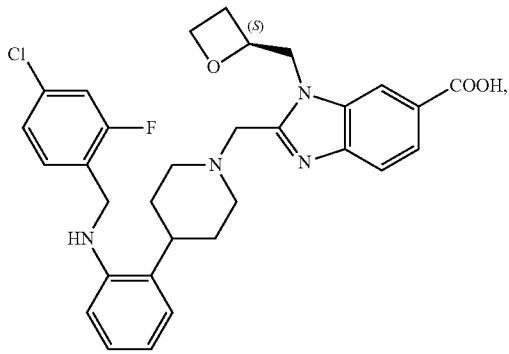
16
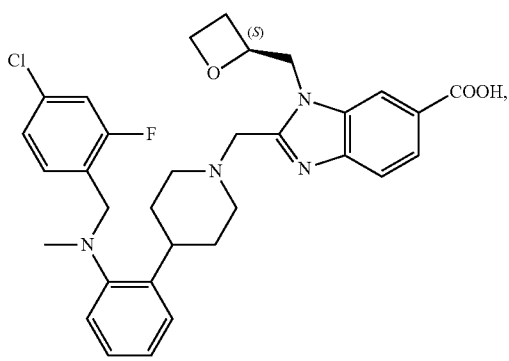
17
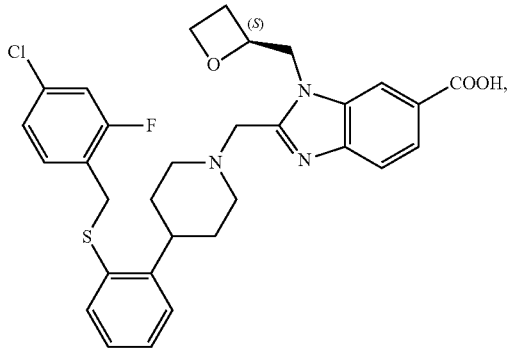
18
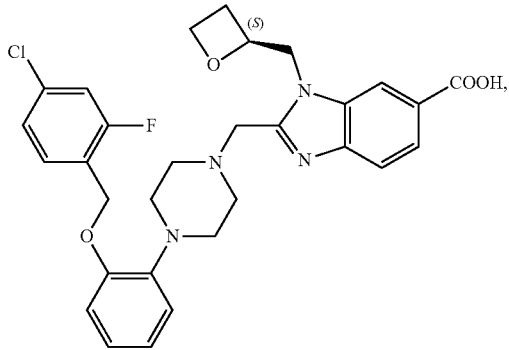

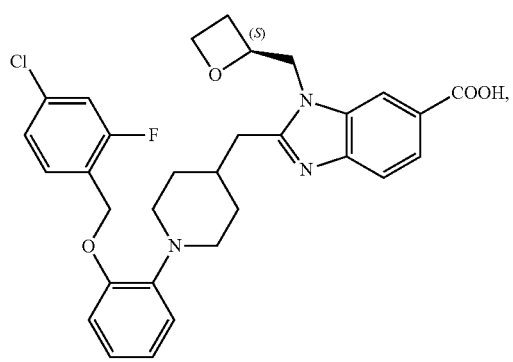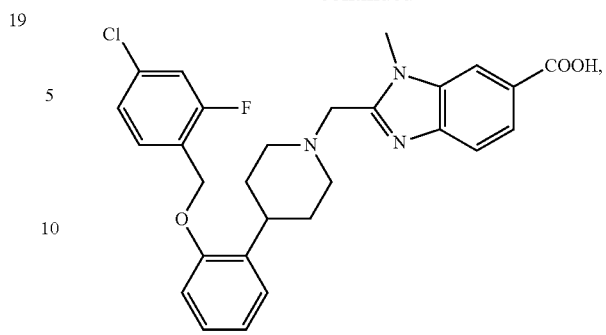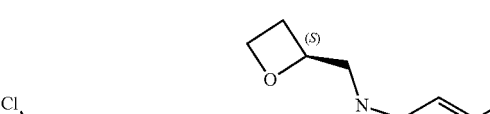

-continued

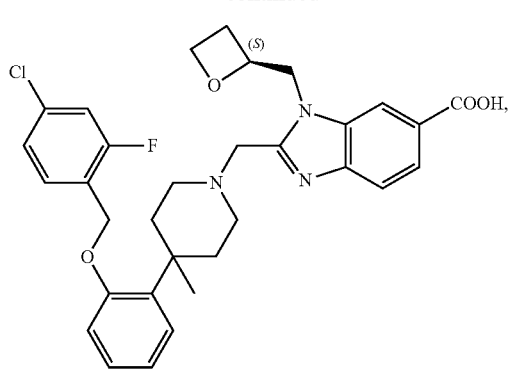

28

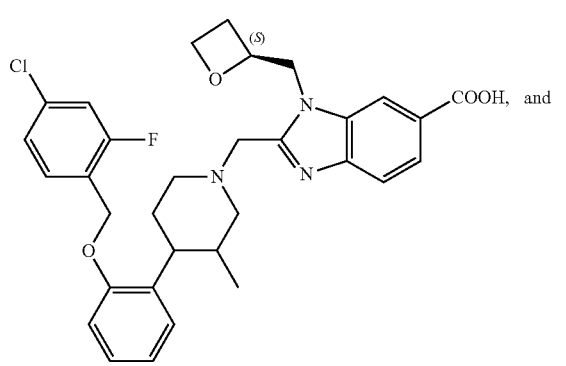

29

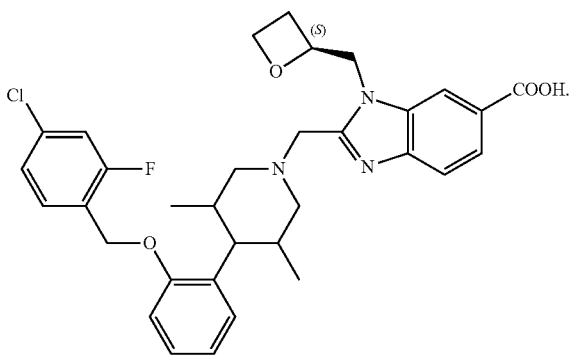

30

8. A pharmaceutical composition, comprising a therapeutically effective amount of the compound or the pharmaceutically acceptable salt thereof according to claim 1 as an active ingredient, and a pharmaceutically acceptable excipient.

9. A method for treating metabolism-related diseases by activating a GLP-1R receptor in a subject in need thereof, comprising: administering the compound or the pharmaceutically acceptable salt thereof according to claim 1 to the subject.

10. The method according to claim 9, wherein the metabolism-related diseases are selected from glucose intolerance, hyperglycemia, dyslipidemia, type 1 diabetes (T1D), type 2 diabetes (T2D), hypertriglyceridemia, syndrome X, insulin resistance, impaired glucose tolerance (IGT), diabetic dyslipidemia, hyperlipidemia, arteriosclerosis, atherosclerosis, hypertension, obesity, non-alcoholic fatty liver, non-alcoholic steatohepatitis, hepatic fibrosis, cirrhosis, and lethargy.

11. A method for treating metabolism-related diseases by activating a GLP-1R receptor in a subject in need thereof, comprising: administering the compound or the pharmaceutically acceptable salt thereof according to claim 7 to the subject.

12. The method according to claim 11, wherein the metabolism-related diseases are selected from glucose intolerance, hyperglycemia, dyslipidemia, type 1 diabetes (T1D), type 2 diabetes (T2D), hypertriglyceridemia, syndrome X, insulin resistance, impaired glucose tolerance (IGT), diabetic dyslipidemia, hyperlipidemia, arteriosclerosis, atherosclerosis, hypertension, obesity, non-alcoholic fatty liver, non-alcoholic steatohepatitis, hepatic fibrosis, cirrhosis, and lethargy.

13. A method for activating a GLP-1R receptor in a subject in need thereof, comprising: administering the compound or the pharmaceutically acceptable salt thereof according to claim 1 to the subject.

14. A method for activating a GLP-1R receptor in a subject in need thereof, comprising: administering the compound or the pharmaceutically acceptable salt thereof according to claim 7 to the subject.

* * * * *